(12) United States Patent
Lawrence et al.

(10) Patent No.: US 8,845,523 B2
(45) Date of Patent: *Sep. 30, 2014

(54) ENDOSCOPE APPARATUS, ACTUATORS, AND METHODS THEREFOR

(75) Inventors: Dale A. Lawrence, Louisville, CO (US); Sutha Aphanuphong, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 371 days.

This patent is subject to a terminal disclaimer.

(21) Appl. No.: 13/336,726

(22) Filed: Dec. 23, 2011

(65) Prior Publication Data

US 2012/0172666 A1    Jul. 5, 2012

Related U.S. Application Data

(63) Continuation of application No. 11/400,065, filed on Apr. 7, 2006, now Pat. No. 8,123,678.

(51) Int. Cl.
| | | |
|---|---|---|
| *A61B 1/00* | (2006.01) | |
| *A61B 1/012* | (2006.01) | |
| *A61B 1/267* | (2006.01) | |
| *A61B 17/00* | (2006.01) | |

(52) U.S. Cl.
CPC .............. *A61B 1/2676* (2013.01); *A61B 1/012* (2013.01); *A61B 2017/00867* (2013.01); *A61B 2017/00398* (2013.01); *A61B 2017/003* (2013.01)
USPC ............................ 600/151; 600/143; 600/146

(58) Field of Classification Search
USPC ........................................................ 600/151
See application file for complete search history.

(56) References Cited

U.S. PATENT DOCUMENTS

| | | | |
|---|---|---|---|
| 4,368,730 A | 1/1983 | Sharrock | |
| 4,427,000 A | 1/1984 | Ueda | |
| 4,543,090 A | 9/1985 | McCoy | |
| 4,742,817 A | 5/1988 | Kawashima | |
| 4,799,474 A | 1/1989 | Ueda | |

(Continued)

FOREIGN PATENT DOCUMENTS

JP          11-048171          2/1999

OTHER PUBLICATIONS

Aramaki (1995) IEEE, pp. 115-120, Micro Machine and Human Science MHS '95. Proceedings of the Sixth International Symposium on Nagoya Japan, "Tube Type Micro Manipulator Using Shape Memory Alloy (SMA)".

(Continued)

*Primary Examiner* — Matthew J Kasztejna
(74) *Attorney, Agent, or Firm* — Sheridan Law, LLC

(57) ABSTRACT

There is disclosed a MicroFlex Scope (MFS). The MFS is a dexterous endoscope providing access, direct visualization, tissue sampling, and treatment, of body lumens. In one embodiment, the distal end of the MFS is an ultra-flexible tip that comprises a plurality of thin, curved shape memory alloy (SMA) actuator elements attached to at least one structural skeleton, a coil spring skeleton or hinge structure. The SMA actuator elements in each structural skeleton segment are indirectly heated by a heater element and produce force in response to their temperature relative to specific thresholds. In configurations comprising a plurality of actuator elements, multiplexing/demultiplexing of heating currents and sensor voltages may be accomplished via a parallel bus and demultiplexing circuit. In this regard, a demultiplexing circuit using standard microelectronic fabrication techniques may be designed to achieve individual sensing and control over each actuator element.

7 Claims, 14 Drawing Sheets

(56) References Cited

U.S. PATENT DOCUMENTS

| | | | |
|---|---|---|---|
| 4,884,557 | A | 12/1989 | Takehana |
| 4,930,494 | A | 6/1990 | Takehana |
| 4,977,886 | A | 12/1990 | Takehana |
| 5,405,337 | A | 4/1995 | Maynard |
| 5,624,380 | A | 4/1997 | Takayama |
| 5,679,216 | A | 10/1997 | Takayama |
| 5,897,488 | A | 4/1999 | Ueda |
| 5,996,346 | A | 12/1999 | Maynard |
| 6,072,154 | A | 6/2000 | Maynard |
| 6,169,269 | B1 | 1/2001 | Maynard |
| 6,278,084 | B1 | 8/2001 | Maynard |
| 6,425,418 | B1 | 7/2002 | Maeda |
| 6,447,478 | B1 | 9/2002 | Maynard |
| 6,672,338 | B1 | 1/2004 | Esashi |
| 6,679,836 | B2 | 1/2004 | Couvillon, Jr. |
| 6,770,027 | B2 | 8/2004 | Banik et al. |
| 6,832,478 | B2 | 12/2004 | Anderson et al. |
| 6,936,015 | B2 | 8/2005 | Esashi |
| 7,223,329 | B2 | 5/2007 | Esashi |
| 8,123,678 | B2 | 2/2012 | Lawrence et al. |
| 2006/0074372 | A1 | 4/2006 | Haga |
| 2007/0037445 | A1 | 2/2007 | Park |
| 2007/0083084 | A1 | 4/2007 | Esashi |
| 2009/0009656 | A1 | 1/2009 | Honda et al. |

OTHER PUBLICATIONS

Dario, et al. (1991) IEEE, pp. 171-175, Micro Electro Mechanical Systems Proceedings of an Investigation of Micro Structures Sensors Actuators Machines and Robots Nara Japan "A Miniature Device for Medical Intracavitary Intervention".
Dario, et al., (1997) Proceedings of the 1997 IEEE International Conference on Robotics and Automation, pp. 1573-1579, Albuquerque New Mexico, "A Miniature Steerable End-Effector for Application in an Integrated System for Computer-Assisted Arthroscopy".
Haga, et al., (1998) IEEE, Micro Electro Mechanical Systems MEMS 98 Proceedings of the Eleventh Annual International Workshop on Heidelberg Germany, "Small Diameter Active Catheter Using Shape Memory Alloy".
Haga, et al., (2000) IEEE, pp. 181-186, Micro Electro Mechanical Systems MEMS 2000 The Thirteenth Annual International Conference on Miyazaki Japan, "Bending, Torsional and Extending Active Catheter Assembled Using Electroplating".
Haga, et al., (2000) Sensors Update 8(1):147-186, "Multi-Functional Active Catheter".
Haga, et al., (2002) World Automation Congress Proceedings of the 5th Biannual, pp. 291-296, "Active Catheter, Active Guide Wire and Related Sensor Systems".
Haga & Esashi (2004) Proceedings of the IEEE 92:98-114, "Biomedical Microsystems for Minimally Invasive Diagnosis and Treatment".
Haga, et al., (2005) Proceedings of the 3rd Annual International IEEEEMBS Special Topic Conference on Microtechnologies in Medicine and Biology, Kahuku Oahu Hawaii, pp. 249-252, "Active Bending Ileus Tube Using Shape Memory Alloy for Treatment of Intestinal Obstruction".
Haga, et al. (2005) Smart Materials and Structures 14:S266-S272, "Medical and Welfare Applications of Shape Memory Alloy Microcoil Actuators".

Haga, et al. (2006) Minimally Invasive Therapy 15:218-225, "Minimally Invasive Diagnostics and Treatment Using Micro/Nano Machining".
Ikuta, et al., (1988) IEEE, pp. 427-430, Robotics and Automation IEEE International Conference on Philadelphia PA, "Shape Memory Alloy Servo Actuator System with Electric Resistance Feedback and Application for Active Endoscope".
Kaneko, et al. (1996) Journal of Intelligent Material Systems and Structures 7:311-335 "Multi-Freedom Tube Type Manipulator with SMA Plate".
Lim, et al., (1995) IEEE pp. 116-121, Micro Electro Mechanical Systems MEMS '95 Proceedings of Amsterdam Netherlands 1995 Geunbae Lim, "Active Catheter with Multi-Link Structure Based on Silicon Micromachining".
Lim, et al. (1996) Sensors and Actuators 56:113-121, "Future of Active Catheters".
Maeda, et al., (1996) IEEE pp. 290-295, Micro Electro Mechanical Systems MEMS '96 Proceedings of the Ninth Annual International Workshop on San Diego CA, "Active Endoscope with SMA (Shape Memory Alloy) Coil Springs".
Makishi, et al., (2006) BioRob 2006, Biomedical Robotics and Biomechatronics, The First IEERAS-EMBS International Conference, "Active Bending Electric Endoscope Using Shape Memory Alloy Coil Actuators".
Park & Esashi (1999) Journal of Microelectromechanical Systems 8:349-357, "A Multilink Active Catheter with Polyimide-Based Integrated CMOS Interface Circuits".
Takizawa, et al. (1999) IEEE pp. 412-417, Micro Electro Mechanical Systems MEMS '99 The Twelfth IEEE International Conference on Orlando FL. "Development of a Microfine Active Bending Catheter Equipped with MIF Tactile Sensors".
Arai, et al., (1995) SICE '95. Proceedings of the 34th SICE Annual Conference. International Session Papers, Jul. 26-28, pp. 1383-1386, "Feeback Linearization for SMA (Shape Memory Alloy)".
Aramaki, et al., (1995) IEEE, Sixth International Symposium on Micro Machine and Human Science, (Month Unknown) pp. 115-120, "Tube Type Micro Manipulator Using Shape Memory Alloy (SMA)".
Fukuda, et al., (1994) Proc. IEEE Conference on Robotics and Automation (Month Unknown) pp. 2290-2295, "Micro Active Catheter System with Multi Degrees of Freedom".
Langelaar and Van Keulen (2004) 45th AIAA/ASME/ASCE/AHS/ ASC Structures, Structural Dynamics & Materials Conference Apr. 19-22, Palm Springs, California, pp. 1-16, "Modeling of a Shape Memory Alloy Active Catheter".
Mineta, et al., (2001) Sensors and Actuators A 88:112-120, "Batch Fabricated at Meandering Shape Memory Alloy Actuator for Active Catheter" (Month Unknown).
Mineta (2004) J. Micromech. Microeng. 14:76-80, "Electrochemical Etching of a Shape Memory Alloy Using New Electrolyte Solutions", published online Aug. 18, 2003.
Tung, et al., (2006) Biomedical Robotics and Biomechatronics, BioRob. The First IEEE/RAS-EMBS International Conference on Pisa, Italy, Feb. 20-22, pp. 775-780, "Design and Fabrication of Tubular Shape Memory Alloy Actuators for Active Catheters".
Wang, et al., (2004) Materials and Design 25:699-703, "Characteristics of Two-Way Shape Memory TiNi Springs Driven by Electrical Current", published online Apr. 23, 2004.

1210 SMA layer
    1211 Cut to size and clean blank SMA sheet material
    1212 Laminate both sides with Riston resist
    1213 Place in frame containing aligned photomask patterns for front and back side
    1214 Expose and develop patterns
    1215 Etch patterns in HNA etchant, timing etch to achieve required thickness profile
    1216 Strip remaining etch resist
1220 Heater/sensor/bus (no demultiplexer chip)
    1221 Cut brass sheet stock into circular disk substrates
    1222 Polish both sides of brass substrates
    1223 Clean substrates
    1224 Spin on polyimide 1 layer and hard-bake cure
    1225 Spin on negative photoresist and soft-bake cure
    1226 Position in mask aligner with heater1/bus photomask
    1227 Expose and develop pattern
    1228 Condition surface with O2 RIE
    1229 Sputter layer of amorphous Al
    1230 Liftoff Al pattern in Acetone ultrasonic cleaner
    1231 Spin on polyimide adhesion promoter and spin dry
    1232 Spin on polyimide 2 layer, hard-bake cure
    1233 Spin on positive etch resist and soft bake cure
    1234 Position in mask aligner with polyimide 2 photomask
    1235 Expose and develop pattern
    1236 Etch polyimide pattern in O2 RIE
    1237 Strip photoresist
    1238 Spin on negative photoresist and soft-bake cure
    1239 Position in mask aligner with heater 2 photomask
    1240 Expose and develop pattern
    1241 Condition surface in O2 RIE
    1242 Sputter layer of amorphous Al
    1243 Liftoff Al pattern in Acetone ultrasonic cleaner
1230 Heater/sensor/bus (with demultiplexer)
    1231 Construct demultiplexer circuits on silicon wafer (see procedure in Figure 13)
    1232 Spin on polyimide adhesion promoter and spin dry
    1233 Continue as in procedure 120 starting with step 124
1240 Bond SMA to Heater/sensor
    1241 Spin on uncured silicone gel onto heater/sensor Al pattern 2
    1242 Bake to cure
    1243 Fix patterned SMA onto glass plate using temporary adhesive on handling frame
    1244 Position SMA over heater/sensor substrate in mask aligner
    1245 Press together to bond
    1246 Remove assembly from glass plate with adhesive solvent
1250 Remove Substrate (no demultiplexer)
    1251 Spin on photoresist to protect front side of assembly and soft-bake
    1252 Immerse in FeCl3 etchant to completely remove brass substrate
    1253 Handle released lattice by handling frame to clean and strip photoresist
1260 Remove Substrate (with demultiplexer)
    1261 Place substrate in back-side etch apparatus
    1262 Fill with KOH etchant and enable heater and stirrer
    1263 Etch until substrate is completely removed around chips
    1264 Empty KOH from apparatus
    1265 Remove lattice via handling frame and rinse

FIG.12

Substrate wafer: N-type silicon, orientation <100>, doped to 2-5 .cm, total thickness approximately 280 m.

1310 Grow thick SiO2 (field oxide) on Si Wafer using wet oxidation in furnace
   1320 Front and Back alignment
        1321 Align front and back registration masks on both sides of a wafer pouch, adhesively bond to fix alignment
        1322 Spin on negative photoresist on back side of wafer and softbake photoresist
        1323 Spin on negative photoresist on front side of wafer and softbake photoresist
        1324 Insert wafer into alignment pouch and expose alignment pattern on front and back side of wafer
        1325 Hard bake photoresist
        1326 Develop photoresist patterns, remove residue in O2 RIE.
        1327 Etch the alignment marks through the field oxide in Buffered Oxide Etchant (BOE)
        1328 Strip the photoresist
   1330 Diffusion
        1331 Spin on positive photoresist on the back side, softbake.
        1332 Spin on negative photoresist on front side, softbake.
        1333 Align the diffusion pattern on front side using oxide alignment marks
        1334 Hardbake, develop front side pattern, and clean photoresist residue in O2 RIE.
        1335 Etch the front side oxide pattern with BOE
        1336 Remove photoresist on front and back of wafer
        1337 Deposit boron dopant in diffusion furnace
   1340 Gate Oxide
        1341 Spin on negative photoresist on back side of wafer, softbake
        1342 Spin on negative photoresist on front side of wafer, softbake
        1343 Expose the front pattern (gate oxide) and back pattern (etch protection ring)
        1344 Hardbake, develop patterns, and clean photoresist residue in O2 RIE
        1345 Open gate oxide and back side ring with BOE
        1346 Strip photoresist on front and back.
        1347 Grow thin oxide on front and back in wet oxidation furnace
   1350 Via holes
        1351 Spin on positive photoresist on back side, softbake
        1352 Spin on negative photoresist on front side, softbake
        1353 Expose via hole pattern on front side
        1354 Develop pattern and clean with O2 RIE
        1355 Open via hole pattern with BOE
        1356 Remove photoresist from front side
   1360 Metal deposition
        1361 Sputter aluminum on front side
        1362 Spin on Positive photoresist on front side, softbake
        1363 Expose aluminum pattern, Develop and clean photoresist residue in O2 RIE
        1364 Etch aluminum pattern in Al etchant
        1365 Remove photoresist from front and back
        1366 Anneal Aluminum in furnace
   1370 Pattern the back side for backside chip release etch
        1371 Spin on positive photoresist on front side, softbake
        1372 Spin on negative photoresist on back side, softbake
        1373 Expose back side pattern, develop, and clean residue with O2 RIE
        1374 Etch back side SiO2 pattern with BOE
        1375 Remove photoresist

FIG.13

ENDOSCOPE APPARATUS, ACTUATORS, AND METHODS THEREFOR

CROSS-REFERENCE TO RELATED APPLICATION

This is a continuation of pending prior U.S. patent application Ser. No. 11/400,065, filed Apr. 7, 2006 by Dale A. Lawrence, et al. for ENDOSCOPE APPARATUS, ACTUATORS, AND METHODS THEREFOR. The above-identified patent application is hereby incorporated herein by reference.

STATEMENT AS TO RIGHTS TO INVENTIONS MADE UNDER FEDERALLY SPONSORED RESEARCH OR DEVELOPMENT

The government has rights in this invention arising from National Institutes of Health STTR Grant Nos. 1 R41 HL083331-01 and 1 R41AI063892-01, that partially funded the research leading to this invention.

BACKGROUND OF THE INVENTION

In recent years there has been increasing use of endoscopes for minimally invasive treatment and diagnosis. For example, endoscopes are often used in diagnostic procedures in an attempt to visualize and diagnose problems in the sinus structures, as well as in sinus surgeries. Due to its proximity to sensitive orbital and cerebral structures, access, visualization, and surgeon confidence all factor into clinical efficacy, patient safety and minimizing complications in diagnosing and performing surgery in this challenging anatomical area. However, current endoscopes, and related instrumentation do not provide the flexibility, dexterity and small enough diameter to access, directly visualize, and effectively perform sensitive procedures throughout all sinus structures.

Chronic sinusitis affects approximately 33 million Americans each year, and has become one of the most prevalent chronic diseases. See Bajracharva H, Hinthorn D. "Sinusitis, Chronic" www.emedicine.com/med/topic2556.htm. Chronic sinusitis is generally characterized as sinusitis lasting longer than 3 months despite treatment, and/or four recurrences of acute sinusitis. The prevalence of chronic sinusitis is likely to grow with increasing pollution, urban sprawl and resistance to antibiotics. See id.

Because of its persistent nature, chronic sinusitis has become a significant cause of morbidity and involves considerable expense to the worldwide health care system. Chronic sinusitis results in 18 to 22 million U.S. physician office visits annually (See "Adult Chronic Rhinosinusitis: Definitions, Diagnosis, Epidemiology, and Pathophysiology," Otolaryngology—Head & Neck Surgery, Supplement, (2003) September: 129: S1-84), and, in 2001, resulted in 1.3 million documented visits to hospital outpatient facilities. See National Hospital Ambulatory Medical Care Survey: 2001 Outpatient Department Summary. It was the most frequently reported chronic disease in the 1993 National Health Interview Survey, affecting 14.7% of the population and was the fifth most common use of antibiotics. See Sinusitis, American Academy of Allergy, Asthma and Immunology, www.aaaai.org/patients/resources/fastfacts/sinusitis.stm. In 2002, Sinusitis accounted for 9% of all pediatric and 21% of all adult antibiotic prescriptions and, thus, contributes to the increasing rate of antibiotic resistance. See "Antimicrobial Treatment Guidelines for Acute Bacterial Rhinosinusitis," Otolaryngology—Head & Neck Surgery Supplement (2004) January; 130:1-49. Untreated sinusitis affects personal productivity and quality of life. It is associated with exacerbation of asthma and serious complications, such as brain abscess and meningitis, which can produce significant morbidity and mortality. See Bajracharva H, Hinthorn D. "Sinusitis, Chronic" www.e-medicine.com/med/topic2556.htm. While some individuals can be successfully treated with medications, others require surgery.

Millions of diagnostic procedures are conducted each year to attempt to visualize and diagnose problems in the sinus structures. In 2001, approximately 200,000 sinus surgeries were performed in the U.S. See id. The surgeries were performed to treat chronic sinusitis, as well as for excision of tumors and polyps, cerebrospinal fluid (CSF) leak closure, orbital and optic nerve decompression, dacryocystorhinostomy, choanal atresia repair, foreign body removal and epistaxis repair. See Patel A, Vartanian J, Guzman Portugal L. "Functional Endoscopic Sinus Surgery" www.emedicine.com/ent/topic758.htm. The difficulty visualizing and accessing certain areas of the sinus structures, particularly the frontal and the ethmoid sinuses, the proximity of the sinus to sensitive structures, such as the orbit and neurovascular structures, and the presence of abnormal growths or anatomy can cause sinus surgery to be challenging, time consuming, and subject to serious complications. Complications can include: orbital injury or hematoma; bleeding; infection; synechiae formation; CSF leaks; direct brain injury; denuded bone resulting in delayed healing; and diplopia. See Patel A, Vartanian J, Guzman Portugal L. "Functional Endoscopic Sinus Surgery" www.emedicine.com/ent/topic758.htm; Rombout J, deVries N. "Complication in Sinus Surgery and new Classification Proposal." American Journal of Rhinology (2001) 25:280-286; Kennedy D. "Functional Endoscopic Sinus Surgery: Concepts, Surgical Indications, and Instrumentation," Diseases of the Sinuses, Elsevier, 2000, pp. 197-210.

While the incidence of major complications during sinus surgery is low (see Rombout J, deVries N. "Complication in Sinus Surgery and new Classification Proposal."American Journal of Rhinology (2001) 25:280-286), complications such as orbital damage and CSF leaks can cause significant morbidity when they do occur. See Rene C, Rose G, Letnall R, Moseley I. "Major orbital complications of endoscopic sinus surgery" British Journal of Ophthalmology (2001) May 85:598-603. In surgically challenging frontal sinusotomy procedures, damaging exploration or inadvertent stripping of mucosa can result in prolonged morbidity and multiple surgical procedures. See Kennedy D. "Functional Endoscopic Sinus Surgery: Concepts, Surgical Indications, and Instrumentation," Diseases of the Sinuses, Elsevier, 2000, pp. 197-210.

The second largest cause of failure in endoscopic maxillary sinus surgery identified in Richtsmeier's study was ethmoid/frontal disease that couldn't be visualized on a CT scan. See Richtsmeier W J. "Top 10 Reasons for Endoscopic Maxillary Sinus Surgery Failure," Laryngoscope (2001) November 111:1952-6. Other studies have highlighted the role of incomplete ethmoid dissection and post-operative scarring in the frontal and ethmoid sinuses as important factors in surgical failure. See Ramadan H. "Surgical Causes of Failure in Endoscopic Sinus Surgery," Laryngoscope 1999; 109:27-9; Shah, N. "Functional Endoscopic Sinus Surgery," www.bhj.org/journal/1999_4104-Oct99/SP_659.HTM. Direct access, clear visualization, and surgeon confidence can all affect outcomes. As such, improved endoscopes are needed that would be smaller, more dextrous, more flexible and allow the physician greater access, visualization and the ability to perform procedures in all of the sinus structures.

Bronchoscopy using endoscopes is also a proven method of directly visualizing the airways of the lung and sampling suspicious tissue. However, current diameters of endoscopes (e.g., ranging from 2.2 mm ultra thin visualization only scopes up to 6.2 mm) prevents access and use in over half the area of the lung. While other forms of testing have evolved (laser induced fluorescence endoscope (LIFE) airway imaging, endobronchial ultrasound, virtual bronchoscopy, spiral CT, CT with nodule enhancement and PET scan), none of the methods offer the unique and significant advantages of conventional bronchoscopy, i.e., direct visualization for accurate location, and collection of tissue samples with minimal safety concerns.

In the United States, the new, diagnosed cases of cancer of the lung and bronchus were estimated at approximately 174,000 in 2003. See Jemal A, Tiwari R, Murray T, et al. Cancer statistics, 2004. *CA Cancer J Clin* (2004) 54: 8-29. U.S. populations of current and ex-smokers (50 million each) make it probable that this significant health problem will continue. See American Cancer Society. (1999) *Cancer Facts and Figures,* 1999. American Cancer Society Atlanta, Ga.

Lung cancer is the most common cause of cancer deaths in the U.S., accounting for more deaths in 2000 than from prostate, breast, and colorectal cancer combined. Less than 15% of patients survive 5 years after diagnosis. The poor prognosis is largely attributable to the lack of effective early detection methods and the inability to cure metastatic disease. Early diagnosis and treatment of lung cancer can significantly improve the patient's chances of survival. See Naruke, T, Tsuchiya, R, Kondo, H, et at (1997) Implications of staging in lung cancer. *Chest* 112(suppl) 4,242S-248S; Mountain, C F, Dresler, C M (1997) Regional lymph node classification for lung cancer staging. *Chest* 111, 1718-1723. Patients with the most favorable clinical stage, IA disease, have a 5-year survival of about 60%, while those with more advanced disease, clinical stage II-IV, have 5-year survival rates ranging from 40% to less than 5%.

Clearly, early identification and intervention are key to improving cure rates. Currently, however, over two-thirds of the patients diagnosed have regional lymph-node involvement or distant disease at diagnosis. See Ihde D.C. Chemotherapy of lung cancer, *N. Engl. J. Med.,* 327: 1434-1441, 1992. The solution requires a shift in the therapeutic paradigm from targeting advanced clinically manifest lung cancer to identifying asymptomatic, preinvasive and early-invasive lesions, coupled with accurate diagnosis and staging.

Bronchoscopy is one of the most commonly used diagnostic and therapeutic procedures in pulmonology, and is routinely used to screen a subgroup of patients at high risk for lung cancer, including those with a) risk factors (emphysema, family history, environmental exposures), b) atypical sputum cytology, or c) suspicious chest x-ray. These procedures are well-tolerated by most patients using local anesthesia and conscious sedation, with exam times of 20-45 minutes, which refined techniques can extend to 60-120 minutes without compromising patient comfort. Direct visualization of the airways can localize potential abnormalities of the tracheobronchial mucosa. The characteristics of these abnormalities (color, stiffness, vascularization, smooth margins, etc.) help to establish the diagnosis and direct treatment. The channels of the flexible bronchoscope support the removal of secretions and samples through bronchial washing, brushing, and biopsy to establish histologic diagnosis, with an average diagnostic yield of 90% for central lung cancers. See Mazzone, P., Jain, P., Arroliga, A. C., Matthay, R. A., Bronchoscopy and Needle Biopsy Techniques for Diagnosis and Staging of Lung Cancer. *Clinics in Chest Medicine.* 23:137-158, 2002; C. Agusti, A. Xaubet, "Bronchoscopic procedures in the new millennium" www.personal.u-net.com/~ersj/Buyers%20Guide%20for%20the%20Internet/agusti37-38.html.htm.

The current size (diameter) of conventional bronchoscopes have limited the ability to access the majority of the lung. Reductions in the size of the developmental bronchoscope have demonstrated success in expanding its reach and capabilities. See Schoenfeld, N., et. al., Ultrathin Bronchoscopy as a New Tool in the Diagnosis of Peripheral Lung Lesions, *Lung Cancer Frontiers*, No. 9, October 2000; Rooney, C. P., Wolf, K., McLennan, G. Ultrathin Bronchoscopy as an Adjunct to Standard Bronchoscopy in the Diagnosis of Peripheral Lung Lesions, *Respiration,* 69:1, 2002.

Although desirable, it is currently impractical to use bronchoscopy to screen the general population or to examine small bronchioles. However, since bronchoscopy is currently part of a routine protocol for high risk populations, it would be desirable to expand access into the bronchial tree to more areas where lung cancer predominates, such as the upper lobes, or to targeted areas identified by CT. See Byers T E, Vena J E, Rzepka T F. "Predilection of Lung Cancer for the Upper Lobes: An Epidemiologic Inquiry," *J Natl Cancer Inst.* 1984 June; 72(6):1271-5. Thus, additional improvements in bronchoscopes are needed.

Some recent efforts have focused on developing endoscopes with active catheters in which a shape memory alloy (SMA) that is deformable when electrically heated is utilized as actuator elements. For example, JP Laid-Open publication No. H11-48171 published Feb. 23, 1999 proposes an active catheter of an outer skeleton type in which a liner coil is disposed outside of a plurality of coiled actuators which are made of a shape memory alloy. The SMA actuators are directly electrically energized to permit the active catheter to be bent or flexed. U.S. Pat. No. 6,672,338 also discloses an active catheter having a linear coil forming an elastically deformable skeletal structure and a coil spring actuator made of shape memory alloy. However, improvements in endoscope design and actuation are still needed.

BRIEF SUMMARY OF THE INVENTION

The present invention is generally directed to actuator elements, actuated structural skeletons, endoscope apparatus including such actuator elements, and methods of using and making the same.

In a first aspect, an actuator element is provided. In certain embodiments, the actuator elements of the inventions generally comprise: a flat shape memory alloy (SMA) layer adapted to exhibit a variation in bend state corresponding to a variation in temperature of the SMA layer; an integrated heater/sensor layer interfaced with said SMA layer; and a demultiplexing circuit and parallel bus interfaced with said heater/sensor layer. The heat/sensor layer is adapted to indirectly heat the SMA layer upon application of current to the heater/sensor layer, to sense the temperature and bend state of the SMA layer, and to produce a voltage in proportion to the sensed temperature and bend state of the SMA layer. Further, the demultiplexing circuit and parallel bus are adapted to allow for connection of multiple actuator elements thereby enabling communication and control of individual actuator elements when multiplexed with a plurality of actuator elements. In some embodiments, the parallel bus comprises a multi-wire flex cable bus system configured to interconnect multiple actuator elements.

In another aspect, a method of making an actuator element of the invention is provided. The method generally comprises: providing a SMA layer temporarily fixed to a first carrier substrate; and providing an integrated heater/sensor/demultiplexer layer fixed to a second silicon substrate. The two substrates are bonded face-to-face using a silicone gel adhesive, and the second silicon substrate is removed from the heater/sensor layer via silicon back-side etch process. The adhesive securing the cured SMA/heater/sensor/demuliplexer alignment to the first silicon substrate is removed to thereby result in a completed SMA/heater/sensor/demultiplexer actuator element.

In certain embodiments, the demultiplexing circuit and parallel bus comprises a multi-wire flex cable bus, demultiplexing circuit chips, and heater/sensor elements. In such embodiments, the method for making the demultiplexing circuit chips, parallel bus, and heater/sensor layers may optionally comprise: constructing the demultiplexing circuits on a silicon substrate using metal oxide semiconductor processes, such as photolithographic patterning, oxidation, dopant diffusion or implantation, and metal sputtering or evaporation; depositing and patterning alternate layers of polyimide and metal over said demultiplexing circuits to thereby provide said multi-wire bus and heater/sensor layers; and selectively removing the silicon substrate via back-side etching to thereby provide separate demultiplexing circuits and heater/sensor layers, connected by the parallel bus.

In yet another aspect of the invention, an actuated coil segment is provided. The actuated coil segments of the invention may comprise: a plurality of shape memory alloy (SMA) actuator elements interconnected via a lattice structure adapted to provide skeleton attachment points; and a coil spring skeleton secured to the plurality of SMA actuator elements via the attachment points of the lattice structure. In certain embodiments, the SMA actuator elements comprise a SMA layer interfaced with an integrated heater/sensor layer configured so as to indirectly heat the SMA layer. The SMA actuator elements may be interconnected in a lattice structure, and the lattice structure is secured to the SMA coil skeleton such that the coil skeleton contacts the lattice structure at attachment pints, and abuts the lattice structure at other load-bearing points.

In yet another aspect, a method of making an actuated coil segment of the invention is provided. Such methods generally comprise: providing a plurality of SMA actuator elements as an interconnected lattice structure to provide skeleton attachment points and providing the SMA coil skeleton located about its exterior perimeter to a copper welding probe and interior copper mandrels adapted to act as resistance welding electrodes; wherein the ends of the SMA coil skeleton are secured to tension fixtures at their distal ends to thereby provide axial tension to the SMA coil skeleton and compression forces between copper electrodes while located on the welding fixture. The SMA coil skeleton located on the welding mandrel is then aligned relative to the SMA actuator lattice structure such that the coil skeleton attachment and load-bearing features interface with the corresponding features on the SMA lattice. The copper mandrel is rolled relative to the SMA actuator lattice structure while selectively energizing the copper mandrel and welding proble at locations corresponding to the skeleton attachments points so as to form spot welds at said attachment points. The proximal ends of the SMA coil skeleton are then released from tension fixtures following formation of said spot welds, thereby allowing the axial tension in the SMA coil skeleton to compress the plurality of SMA actuator elements inward, resulting in a compressed state coil segment.

In yet another aspect of the invention, a microdexterous endoscope apparatus is provided. The endoscope apparatus generally comprises: a catheter having a lumen comprising at least one port in the interior of said lumen; at least one actuated coil segment at the distal end of the catheter comprising at least one port in the interior of said actuated coil segment; a control system configured to monitor and control actuation of at least one coil segment based at least in part on temperature and strain feedback from said actuated coil segment; and an electrical bus traversing the length of the catheter and interfacing with said at least one actuated coil segment and said control system. In certain embodiments, the actuated coil segment comprises a plurality of indirectly heated shape memory alloy (SMA) actuators secured to a SMA coil skeleton, wherein each SMA actuator is adapted to exhibit a variation in bend state corresponding to a variation in temperature of the SMA actuator. Further, the control system is preferably adapted to modulate application of a current to thereby independently control the temperature of the plurality of SMA actuators to achieve a desired bend state based at least in part on a non-linear hysteresis control model using feedback voltages obtained from the SMA actuator via the electrical bus.

In yet other aspects of the invention, methods for the direct visualization of a body lumen are provided. Such methods generally comprise: inserting the catheter of an endoscope of the invention into a subject comprising a body lumen to be visualized; manipulating placement of the distal end of said catheter in the body lumen to be visualized via said at least one actuated coil segment; and directly visualizing said body lumen via the image guide. In certain embodiments, the body lumen is selected from the group consisting of lung airways, bronchial airways, and sinus cavities.

In other aspects, the catheter comprises at least two ports, and the second port comprises a tool configured to sample tissue. In such embodiments, the methods of the inventions may further comprise: manipulating placement of the distal end of said catheter via said at least one actuated coil segment to thereby locate said tissue sampling tool at a desired location; and obtaining a tissue sample via said tissue sampling tool.

In other aspects, the catheter comprises at least three ports, one port for the image guide, one for the tool, and one for vacuum/flush/drug delivery. Again, in such embodiments, the methods of the inventions may further comprise: manipulating placement of the distal end of said catheter via said at least one actuated coil segment to thereby locate said tissue sampling tool at a desired location; and obtaining a tissue sample via said tissue sampling tool.

These and other aspects of the invention will become apparent to those skilled in the art with reference to the detailed description and drawings.

BRIEF DESCRIPTION OF THE DRAWINGS

FIG. 13 outlines an example construction method for demultiplexing circuits on a silicon substrate.

DETAILED DESCRIPTION OF THE INVENTION

Currently, minimally-invasive endoscopic surgery has widespread applications and will continue to evolve into the standard of care as technology improves. Many diagnostic and surgical procedures that involve small spaces and accessibility problems, including head and neck procedures, sinus procedures, lung and airway procedures, neurosurgery, urology, and pediatric and neonatology procedures are likely to benefit from research and advances in endoscopic technology.

For instance, advances in endoscopes and improved external CT guided imaging provide some assistance to the rhinologic surgeon. Without intending to be limited by theory, small, flexible tools that can navigate through the small, tightly curving sinus structures and support direct visualization and direct access would have the following potential benefits: increased patient safety, reduced risk and complications, reduced surgical time.

Again, without limitation, in lung and airway applications, small flexible endoscopes that could reach the peripheral airways could provide: new capability to perform direct visualization and sampling procedures in small airways, requiring minimal additional exam time; thin, highly controllable visual and manipulative access to sites, reducing invasiveness, patient discomfort, recovery time, and risk; capability to perform procedures such as laser therapy, brachytherapy, electrocautery, cryotherapy, photodynamic therapy, placement of airway stents, and balloon dilatation.

I. Introduction

To address current limitations, the present invention provides, in part, a dexterous endoscope apparatus, referred to herein as a MicroFlex Scope (MFS). The MFS is an novel, small diameter, e.g., less than about 1 mm to about 4 mm, about 1 mm to about 3 mm, etc., dexterous endoscope that allows for access, direct visualization, tissue sampling, treatment, etc. of body lumens and adjacent tissue.

Figure 1:
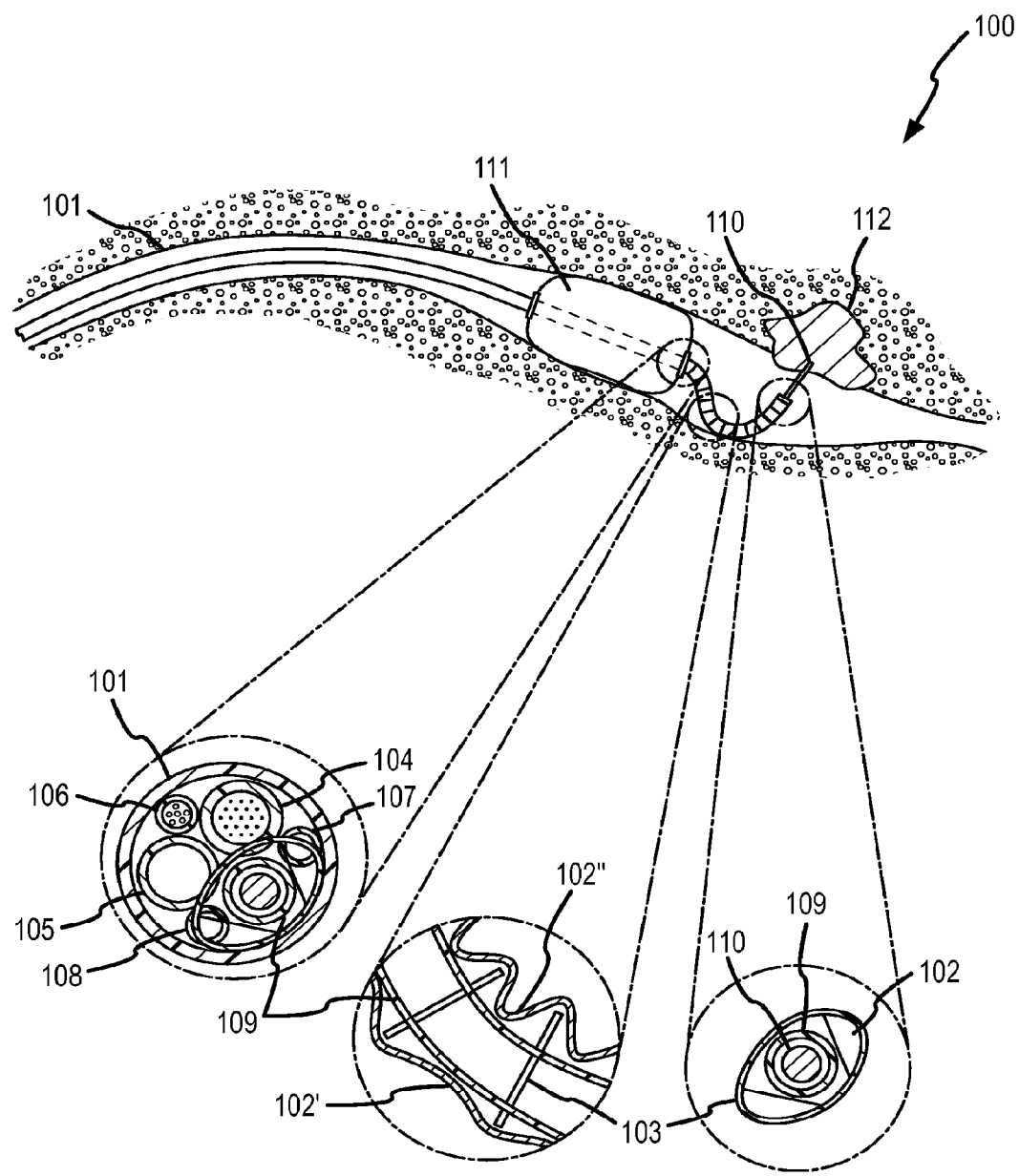
FIG. 1 illustrates a three port embodiment of the MicroFlex Scope with a single tool port passing through the ultra-flexible tip.

In one embodiment (FIG. 1) the distal end of the MFS of the invention is an ultra-flexible tip that comprises a plurality of thin, curved shape memory alloy (SMA) actuator elements 102 attached to at least one structural skeleton, e.g., a coil spring skeleton 103 or hinge structure. The SMA actuator elements in each structural skeleton segment produce force in response to their temperature relative to specific thresholds. The SMA actuator element is compressed by the structural skeleton when its temperature is low, causing each segment to be in a reference state, e.g., curved and short 102" if a coil skeleton is used. Each actuator element can be indirectly heated by a heater element, which causes the actuator to straighten 102' thereby exerting a force on the structural skeleton, e.g., pushing the coil spring apart where the actuator is attached. By individually controlling the temperature in all actuator elements, each segment can be bent in any direction and/or extended. By stacking up segments, the tip of the device can move in any direction with an unprecedented range of motion for its size. FIG. 1 also shows how a fiber optic image guide 104 may be integrated with the actuator elements to enable precise sampling or manipulation of tissue 112 in small spaces. This embodiment also includes a vacuum/flush port 105, illumination fibers 106, an electrical cable for sensing and actuation signals 107, and an internal channel 108 for actuator cooling. An outer sheath 101 encapsulates the endoscope and thermally separates the actuator elements from body tissue. In this embodiment, the tool port 109 is contained in the ultra-flexible tip, enabling a tool 110 to be precisely manipulated by controlling the actuator elements, using visual feedback from the image guide to the surgeon.

Figure 2:
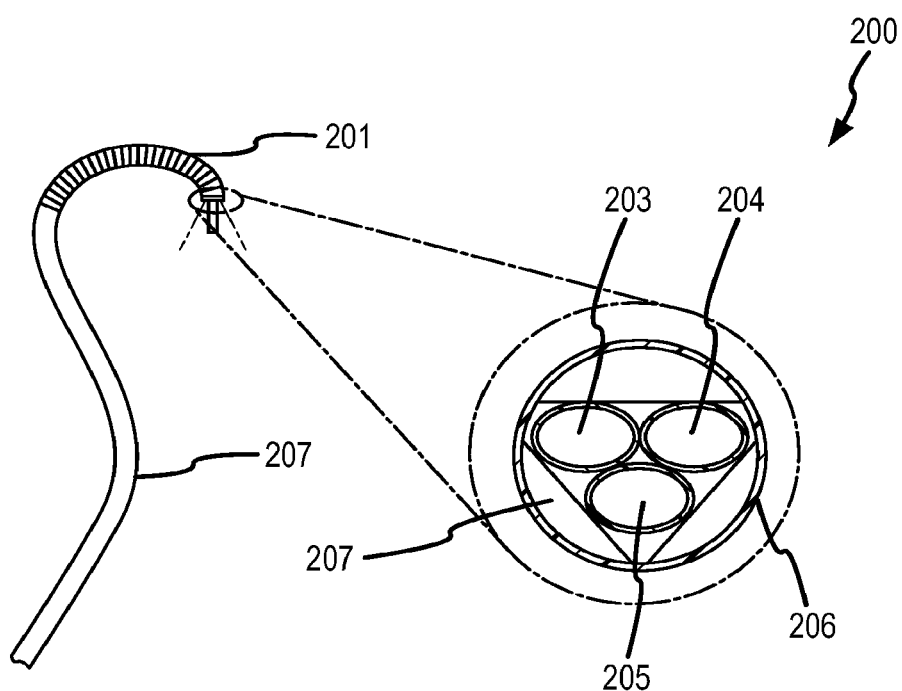
FIG. 2 illustrates a three port embodiment where all three ports pass through the ultra-flexible tip.

The MFS concept is highly modular, enabling a variety of product forms. FIG. 2 shows a highly integrated, multiport MFS scope containing three ports in a carrier catheter 207 and an actuated tip 201. One port 203 contains an image guide, and two ports 204, 205 are general purpose ports for removable tools or vacuum/flush of fluids. This form contains three actuators 202 per segment and a helical coil skeleton spring 206. FIGS. 3-6 show other product forms which may be developed from MFS technology.

Heating of SMA actuator elements may generally be accomplished by direct Joule heating, enabling resistance feedback for position sensing. However, the relatively large cross sectional area of the actuator elements of the invention often require relatively large currents. The correspondingly large connecting wires may generally limit joint bending, thereby reducing dexterity. As such, in accordance with certain embodiments of the invention, indirect heating of the SMA actuator elements is used, wherein a heater element is interfaced with the SMA. Smaller heating currents and connecting wires are therefore required to heat the actuator elements of the invention, thereby enabling a novel integrated temperature and strain sensing concept, described in further detail herein.

In certain embodiments, the heater element may comprise an integrated heater/sensor element adapted to heat the actuator element and to sense the temperature and bend state of the actuator element. In configurations comprising a plurality of actuator elements, multiplexing/demultiplexing of heating currents and sensor voltages may be accomplished via a parallel bus and demultiplexing circuit. In this regard, a demultiplexing circuit using standard metal oxide semiconductor technology may be designed to achieve individual sensing and control over each actuator element.

Without being limited by any particular theory or mode of operation, the MFS designs of the present invention allow for: safe navigation and direct visualization over an increased area of various body lumens; enhanced flexibility and controllability via actuators in the ultra-flexible MFS tip; accurate diagnostics, effective tissue sampling and treatment using the ultra-flexible and actively-controlled MFS tip; and a cost-effective, manufacturable design through innovations in actuation, control, and assembly that uses similar, modular components to construct tools tailored to a variety of applications.

The MFS represents integrated innovations in actuation, sensing, control and assembly at small scales that can produce an advanced generation of scopes that are more flexible and controllable. Due to these design characteristics, MFS is uniquely positioned to make a significant contribution to improving the, e.g., treatment of chronic sinusitis patients, or in the diagnosis and treatment of lung cancer through direct visualization, localization and more accurate sampling of smaller, peripheral lesions. The MFS may also be used to enhance other procedures where a bronchoscope is used, including diagnosis and treatment of infections, diffuse lung diseases, and airway obstructions. The MFS may also benefit other medical specialists who must visualize and maneuver in small spaces, including pediatricians, neurosurgeons, and ENTs. The MFS technology also has potential applications in many other regions of the body, providing enhanced diagnostic access, direct visualization, and enabling new therapeutic procedures.

The following headings are intended for organizational purposes only, and are not intended to limit the scope of the disclosure in any regard.

II. Actuator Elements of the Invention

As described above, the distal end of the MFS of the invention comprises at least one actuated structural skeleton including a plurality of SMA-based actuator elements. The SMA provides superior capability to produce large extension forces over large deformations through a simple bending action. These characteristics support the construction of very small (less than about 1 to about 4 mm, about 1 to about 3 mm, about 1 to about 2 mm, etc. diameter), actively controlled devices that can reach into and maneuver in small, previously inaccessible body lumens and cavities. Because heating/cooling rates, and, thus, motion speeds, increase dramatically as devices are reduced in size, SMA actuation is ideal for small devices. By way of example, required temperature variations are approximately 25° C. for nickel-titanium (NiTi) SMA alloys useful in connection with the present invention. This range can be adjusted to be compatible for body temperature use by specifying alloy composition. Several vendors now specialize in production of NiTi alloy stock in a variety of forms and activation temperatures, as known in the art. However, the invention is not so limited, and any suitable SMA known in the art may be used.

One known drawback of SMA materials in small-scale applications involves issues with position control. These difficulties arise from hysteresis based on the response of the material to temperature and stress conditions. Repeatable and accurate control of actuator position requires that this non-linear hysteresis characteristic be accurately modeled and compensated for in the control system. As described in further detail below, the present invention, in part, address these difficulties by utilizing an innovative method of controlling this hysteresis, using an explicit temperature control loop in conjunction with a proportional-integral (PI) position control law to produce accurate tracking of motion commands.

More particularly, control of the plurality of actuator elements in a multi-segment device may be supported, at least in part, in accordance with the present invention by two aspects. The first is a parallel bus which connects to all actuator elements, with corresponding demultiplexing circuits for each independent actuator to enable individual communication with each actuator and sensor. The second is an integrated heater/sensor element that heats the SMA actuator material by small electric currents, while producing voltages that are proportional to present temperature and bend state. These voltages are read by a computer controller that adjusts heating current to cause the desired motion in the actuator element based on, e.g., the temperature and PI position control loops.

A. Certain Configurations of Actuator Elements

Figure 7:
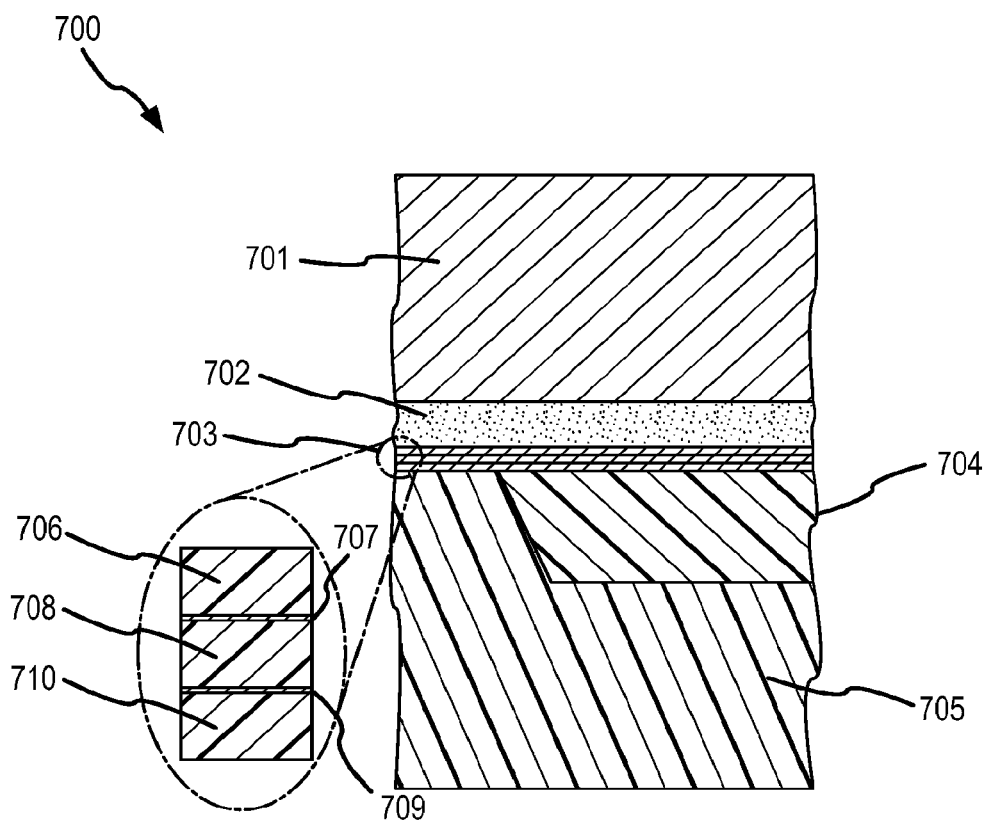
FIG. 7 illustrates a cross-section of an actuator element of the invention

In one aspect, the actuator elements of the invention may comprise: a SMA layer; an integrated heater/sensor layer interfaced with said SMA layer; and a demultiplexing circuit and parallel bus interfaced with said heater/sensor layer. A cross section of an actuator element 700 is shown in FIG. 7. The SMA layer 701 is bonded to the heater/sensor layer 703 by a strain isolation layer 702. The heater sensor layer is a five-layer arrangement of three polyimide layers 706, 708, and 710, sandwiching two metal layers 707 and 709. A demultiplexing chip 704 may be included. The substrate 705 supports the construction of the actuator element, and is removed in final stages of fabrication. In addition, the actuator elements, the actuated structural skeleton, and/or the MFS may be covered by an insulation sheath, so tissue may be shielded from exposure to electrical actuation signals or excessive temperatures when used in vivo. The SMA layer may, for example, range in thickness from about 10 pun to about 60 1.tm, depending on the size of the device and the magnitude of forces desired.

In accordance with the present invention, the SMA layer is adapted to exhibit a variation in bend state corresponding to a variation in temperature of the SMA layer. By way of example, a useful range of motion and force may be obtained with about a 20° C., about a 22° C., about a 24° C., about a 26° C., about a 28° C., or about a 30° C. variation in temperature. In a basic form, this is accomplished by heating the actuators from body temperature (37° C.) to a maximum of, e.g., 67° C. for short periods. If desired, the exterior surface of the SMA layer may be thermally insulated to protect tissue from exposure to excessive temperatures when used in vivo. Alternatively, the exterior surface of the SMA layer may be at least partially interfaced with a closed circuit irrigation system configured to provide a chilled bias temperature state to the SMA layer. For instance, such a cold bias irrigation system may be achieved through a slow infusion of room temperature or chilled sterile saline through the catheter, which may be extracted through the suction port. In other embodiments, such chilled bias may be obtained via use of cooled sterile air, or other suitable liquid or gas. As such, in some embodiments, the SMA layer may comprises a NiTi alloy with a bend state activation temperature between about 17° C. and about 67° C., more particularly, between about 17° C. and about 37° C., between about 17° C. and about 47° C., between about 27° C., and about 47° C., or between about 27° C. and about 57° C.

In certain embodiments, the heat/sensor layer is adapted to heat the SMA layer upon application of current to the heater/sensor layer, and to sense the temperature and bend state of the SMA layer by producing a voltage in proportion to the SMA temperature and bend state. The electrical power necessary to heat the actuator elements may be very low due to their small size. For instance, the maximum power for each actuator may be in the range of about 1-10 mW. The heater/sensor layer may, in some embodiments, comprise two metal layers separated by a dielectric layer. By way of example (FIG. 7), the heater/sensor layer 703 may comprise a polyimide layer 708 deposited between sputtered metal layers 707, 708, e.g. amorphous Aluminum. The metal heater/sensor layers may generally be about 0.1 μm to about 0.2 μm in thickness. and the inner polyimide layer thickness may be between about 0.3 μm and about 1.0 μm, depending on actuator size and corresponding required bend radii. A protective polyimide layer may be include on top 706 and on bottom 710 to comprise the heater/sensor layer.

In certain embodiments, the two layers of the integrated heater/sensor may be connected electrically in series (R1 and R2 in FIG. 8), so that current through the heater/sensor heats the SMA layer for actuation, while the voltage and current are sensed to transduce the SMA layer temperature and bend state via resistance changes. As the SMA layer bends during actuation, a differential strain occurs in the heater/sensor layers, which is sensed via a change in voltage division ratio at the center tap (Sen). This bending strain provides a direct measure of the position, i.e., bend state, of each actuator element, since the heater sensor layer is attached to the SMA with an adhesive which causes the SMA and the heater/sensor layer to have the same bend radius. As the SMA is heated by the heater layers, the change in total resistance due to the material temperature coefficient of resistance is calculated from total voltage (Vdd to Vss) and current (into Vss) in the series connection to provide a measurement of SMA temperature.

Further, the heater/sensor layer may optionally interface with the SMA layer via a strain-isolating adhesive layer, e.g., a silicone adhesive layer 702 (FIG. 7). By way of example, the stain-isolating adhesive layer may be about 5 μm to about 30 μm in thickness, depending on the size of the actuator element. Any suitable strain-isolating adhesive known in the art for such purposes may be used, and the thickness may depend on the particular adhesive selected. The strain-isolating adhesive layer may serve to attenuate the large strain in the SMA layer (about 1 to 4 percent) to levels which prevent fatigue failure in the heater/sensor layer (about 0.1 percent). This strain-isolation layer may also prevent buckling of the heater/sensor layer as the SMA layer bends during actuation.

The silicon demultiplexing chip (FIG. 7,8) and parallel bus may be adapted to allow for connection of multiple actuator elements thereby enabling communication and control of individual actuator elements when multiplexed with a plurality of actuator elements. The parallel bus may preferably comprise a multi-wire flex cable bus system configured to interconnect multiple actuator elements. The interconnection may be a multi-wire bus, e.g. six wires, wherein the multi-wire bus is configured such that one wire supplies heater current, one provides a current return, one provides a strain sensing voltage, one provides a logic ground, and the other two wires provide handshake enable signals. In this embodiment, the enable signals produce a daisy-chain that connects each heater/sensor to the bus through, e.g., FET switches, one at a time, multiplexing sensing and actuation through all actuator elements in the actuated structural skeleton. The demultiplexing circuit is simple, enabling silicon chips to be small enough to be located on each actuator element, enabling high dexterity in a small diameter actuated catheter.

Figure 8:
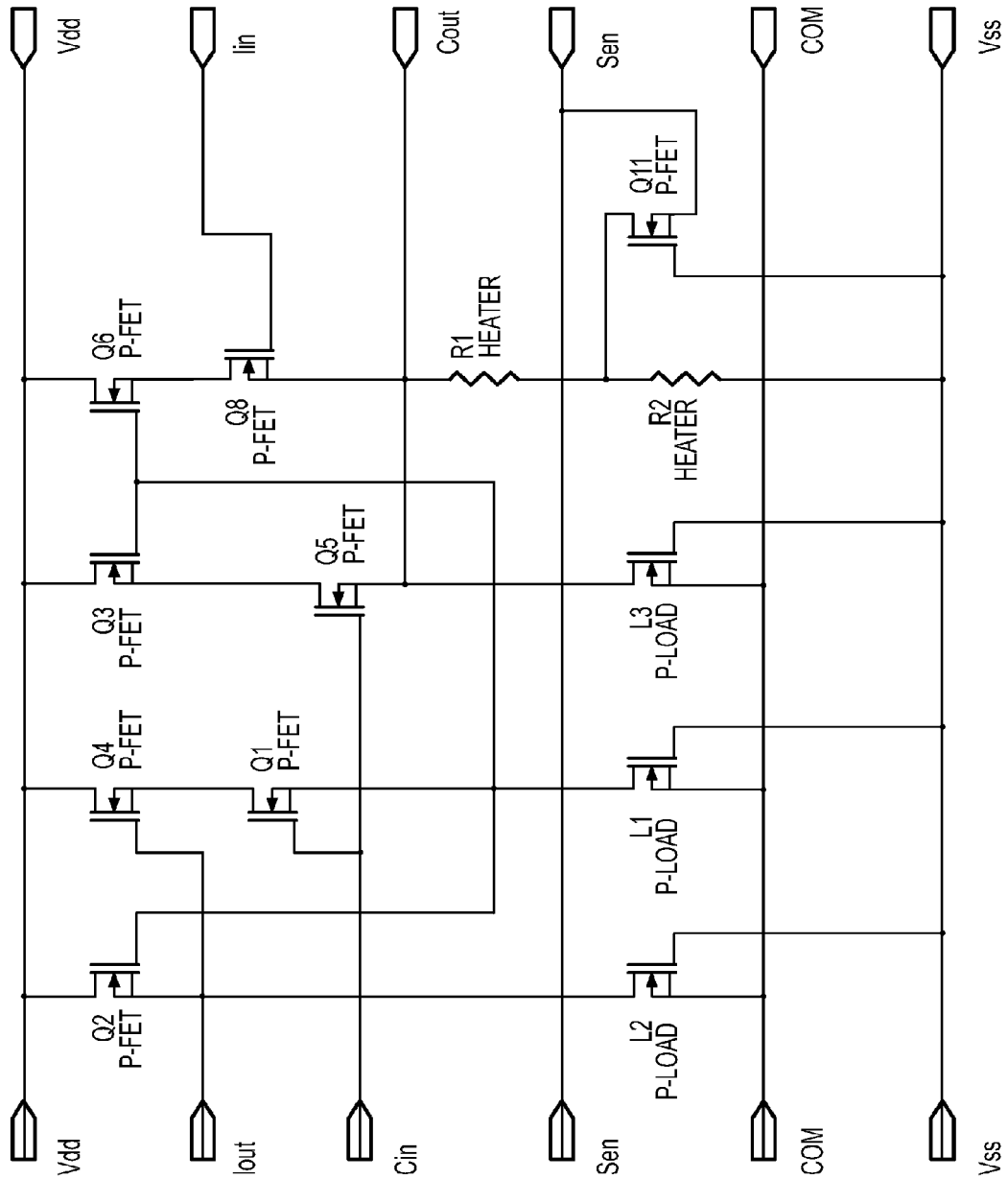
FIG. 8 provides a schematic diagram of one embodiment of a demultiplexer circuit located at each actuator, which enables sensing and control signals to be routed to each actuator element individually.

By way of example, as shown in FIG. 8, a chain-type demultiplexing scheme may be used in which one stage locks out the following stage while it is active, enabling the subsequent stage as it deactivates. This passes active control and sensing connections to each actuator in turn, through the last actuator in the chain. This process is repeated at high rates relative to the heating time constants (e.g., several hundred cycles per second), producing desired average heating and corresponding actuation motions. During each heating cycle, only one actuator heater/sensor is connected to Vss, Vdd, and the center tap sense line Sen via FET switches, enabling each actuator to be individually sensed and controlled.

Figure 10:
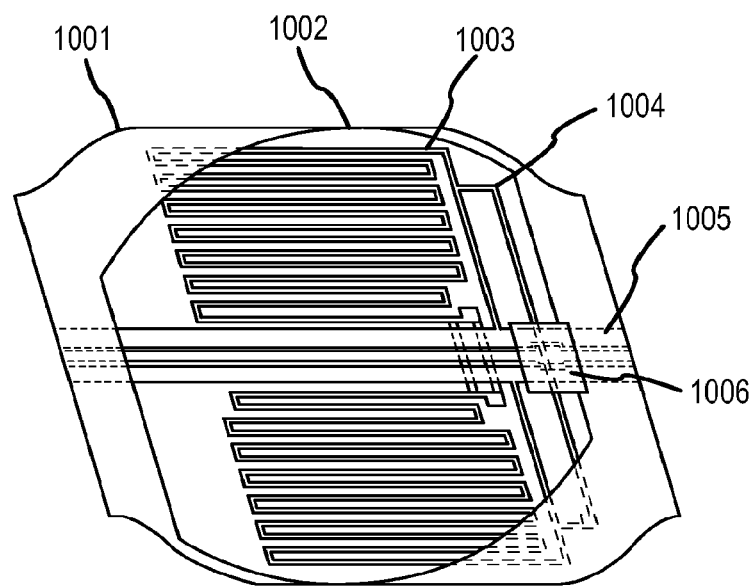
FIG. 10 illustrates a close-up of the layout of each layer comprising an actuator element.

Generally, up to about 30 actuator elements may be served via a single parallel bus, based on the peak currents allowed by power switches and bus conductors currently available in the art. However, the number of actuator elements may vary depending on the exact components used. By way of example, in certain embodiments, the parallel bus will have on-resistances in each segment less than 1/30 of the corresponding actuator heater resistances, and will carry peak currents of at least 30 times the average heater current to enable time-division multiplexing of up to about 30 separate heater elements. Other embodiments may have several actuators ganged together, heating and sensing the several actuators with a single demultiplexer stage. This reduces the number of demultiplexer chips required in the device, but also reduces the number of degrees of freedom that can be independently actuated. In another embodiment, demultiplexer chips are not used. Instead, one, two, or three strings of actuators are operated by separate parallel busses, producing one, two, or three degrees of freedom in motion, but with reduced device complexity and cost. Each string of actuators in this embodiment may include one or more SMA actuator elements, with corresponding heater/sensor layers, connected electrically in parallel. The bus for each string may be simplified, requiring only three wires (Vss, Vdd, and Sen) when demultiplexer chips are not utilized. Such a three wire bus is shown in FIG. 10.

B. Fabrication of Actuator Elements

Efficient manufacturability is of concern in developing new technology. Assembly of complex devices with sub-millimeter components has been technically challenging and cost-prohibitive, unless the entire device can be fabricated using photolithography processes, as in microelectronic circuits and, more recently, microelectromechanical systems (MEMS). However, these devices are limited to a planar 2-dimensional structure. In accordance with the present invention, it has been found that the actuator elements may be fabricated as planar components manufactured using photolithography, and then assembled into 3-dimensional structures using an innovative rolling weld technique described below. These techniques are simple and parallel in nature, supporting low cost, mass manufacturing.

Figure 9:
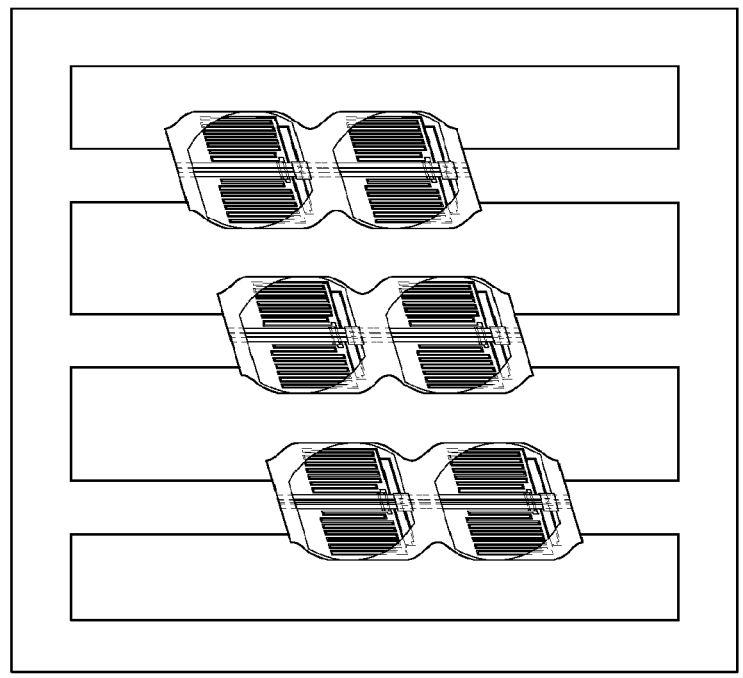
FIG. 9 illustrates a layout of an actuator lattice, containing three strings of two actuator elements each.

In one aspect, a method of making all actuators in the device on a common substrate is provided. The actuators are arranged into a flat multi-element lattice containing one or more strings of actuator elements, and one or more segments of actuators on a common bus in each string. FIG. 9 shows a lattice containing three strings of two segments each. In accordance with one embodiment of the invention, scaling and economic manufacture of the actuator elements described herein may be achieved based, in part, on lithography processes that can produce the small features of the actuator elements of the invention. In an exemplary embodiment illustrated in FIG. 10, the actuator elements may be designed as laminated structures comprising: the SMA layer with a variable thickness produced by a front 1001 and back 1002 etch pattern; a strain-isolating silicone adhesion layer; and an integrated heater/sensor layer 1003, 1004. The interconnecting bus 1005 is also provided on the same layer as the heater 1003. The optional demultiplexing chip 1006 is also shown. Generally, this embodiment requires methods for: providing/fabricating lithography masks for actuator elements; providing/fabricating a patterned SMA layer; providing/fabricating heater/sensor/bus layers; bonding SMA and heater/sensor/bus layers together to form an interconnected actuator lattice; and releasing from carrier substrates as needed. With reference to FIG. 10, an exemplary method (FIG. 12) comprises providing a patterned SMA layer 1210 fixed to a peripheral handling frame. An integrated heater/sensor layer 1220 fixed to a carrier substrate is provided, including a parallel bus fixed to the carrier substrate and electrically connected to the heater/sensor layer, As will be understood by those skilled in the art, the steps of blocks 1210, and 1220 may generally be performed in any order desired.

Moving on, an adhesive silicone layer 1240 is deposited onto the heater/sensor/demultiplexer layer and cured. The SMA layer is then positioned over the heater/sensor/demultiplexer/adhesive layer via a mask aligner such that alignment marks on the two patterns correspond. Once aligned, the SMA layer is pressed onto the heater/sensor layer to effect a permanent bond. The carrier substrate is removed from the assembly by a back-side etch, during which the front-side layers are protected by a temporary etch resist (block 1250). Following substrate removal, the completed actuator lattice is handled via the peripheral SMA handling frame.

Optionally, a demultiplexing circuit may be included (block 1230). SMA thin film patterns in SMA are provided as in block 1210, The heater/sensor/demultiplexer layer, as in block 1220 is a sandwich of polymer (e.g., polyimide) between meander-pattern metal films (e.g., amorphous Al), but now is electrically connected to silicon demultiplexing chips, which are first produced on a silicon substrate (1230). These two layers may then be bonded together with, e.g., a soft silicone adhesive layer (1240), using a mask aligner to position the SMA frame and silicon substrate face-to-face over each other, subsequently forcing them together to effect attachment. The heater/sensor/demultiplexer carrier substrate may then be removed by a patterned, anisotropic silicon back-side etch, using an apparatus which restricts etchant contact to the back side only (block 1260). The finished SMA/heater/sensor elements will generally remain electrically connected to each other in strings, and mechanically connected by the peripheral handling frame.

Fabrication of demultiplexing circuits on a silicon substrate may utilize a variety of foundry processes. The example of FIG. 8 uses a very simple p-type enhancement-mode metal oxide semiconductor process that requires only 4 photolithography masks, as described in detail in FIG. 13. Demultiplexing chips could be produced using other processes, however. For example, the load transistors (L1, L2, L3 in FIG. 8) could be provided by depletion mode devices, or complementary (n-type) devices.

The demultiplexing circuit (FIG. 8) at each actuator is simple, requiring very little silicon area, e.g. 200×200 μm, enabling a small chip to be located at each actuator using the integrated fabrication method discussed above. This preferred method avoids the difficulty of handling and mounting of such small chips. However, the actuator elements are not so limited, and, alternatively, separate manufacturing and subsequent mechanical and electrical connection of the heater/sensor elements to the demultiplexer circuit chips could be utilized, if desired.

In one embodiment, three buses may be fabricated in a lattice structure so that all mechanical and electrical connections to the actuators in a 10 segment, 30 actuator structural skeleton may be accomplished on a single substrate. By way of example, a 10-segment, 3-string lattice with handling frame may be approximately 20 mm by 10 mm, enabling approximately 10 complete MicroFlex sensing/control lattices to be obtained from a single 3 inch diameter silicon wafer.

III. Actuated Structural Skeleton Segments of the Invention

As discussed above, the distal end of an MFS of the invention comprises at least one actuated structural skeleton segment which includes a plurality of actuator elements. The structural skeleton may be any suitable skeleton structure which is capable of supporting a plurality of actuator elements, deforming to a variety of bend states upon heating of the actuator elements, and returning to a base state when the actuator elements are cooled. By way of example, the structural skeleton may be a hinged structure, or preferably an elastic helical coil structure. By varying the cross section diameter of the skeleton wire, as well as the SMA actuator cross section thickness, a wide variation in mechanical properties of the MFS can be obtained. Larger cross sections produce larger force capabilities, but reduced range of motion. Smaller cross sections enable more motion, e.g. smaller catheter bend radii, but lower force capability. Further, the structural skeleton may be comprised of a superelastic material (e.g., NiTi) to further enhance the actuator range of motion, enabling smaller catheter bend radii and enhanced dexterity for a given force capability, because the skeleton wire may be strained well past conventional limits without permanent yielding.

A. Configuration of Certain Actuated Coil Segments

Figure 11:
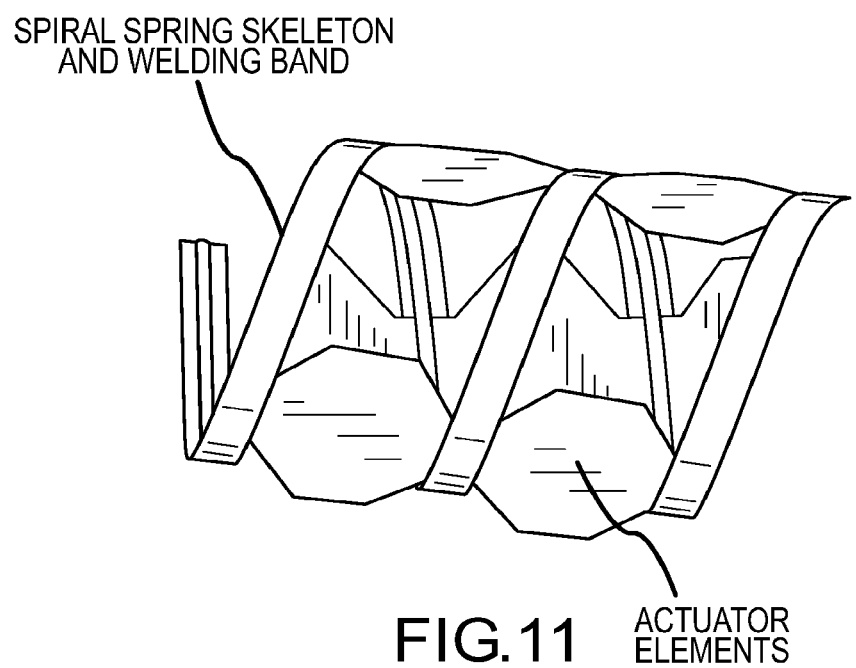
FIG. 11 shows a photograph of a large scale, stainless steel prototype of the actuated coil skeleton FIG. 12 outlines an example construction method for actuator elements.

As such, in one aspect, an actuated coil segment is provided comprising a coil skeleton and a plurality of actuator elements. More particularly, in one embodiment, the actuated coil segment may include: a plurality of SMA actuator elements interconnected via a lattice structure adapted to provide skeleton attachment points, a SMA coil skeleton secured to the plurality of SMA actuator elements via the attachment points, and abuts the lattice structure at other load-bearing points. The actuator elements may be secured to the coil skeleton in any manner known in the art, such as welds, adhesives, bonding, etc. By way of example, when the skeleton spring is superelastic NiTi, the SMA actuator elements may be secured to the SMA coil skeleton via spot welds at the attachment points of the lattice structure, and via the mating of load-bearing features on the coil spring skeleton with corresponding patterns in the SMA lattice structure. When the skeleton is another material, e.g. stainless steel, the SMA actuator lattice may be secured by welding a stainless steel band onto the skeleton, trapping the SMA layer at the attachment points. This is necessary because SMA does not weld well to other materials. FIG. 11 shows a photograph of a prototype that uses the welding band approach. The SMA actuator elements may include a SMA layer interfaced with an integrated heater/sensor layer, as described herein.

The SMA actuator elements may be attached to the SMA coil skeleton in such a manner so as to facilitate bending of the coil skeleton upon actuation of a variation in bend state of an actuator element. For instance, the plurality of actuator elements may be secured to the coil skeleton on the exterior surface of the coil and/or the interior surface of the coil, depending on the particular orientation of the actuator element. In certain embodiments, the SMA actuator elements may be interconnected in a lattice structure, which may be secured to the SMA coil skeleton such that the coil skeleton primarily contacts the lattice structure at the interconnection points. By way of example, the lattice structure may comprise at least two parallel segments of at least three interconnected SMA actuators elements. In other embodiments, the lattice structure comprises at least one series segment of at least one parallel SMA actuator each interconnected via the SMA lattice structure and parallel bus.

B. Fabrication of Actuated Coil Segments

Figure 14:
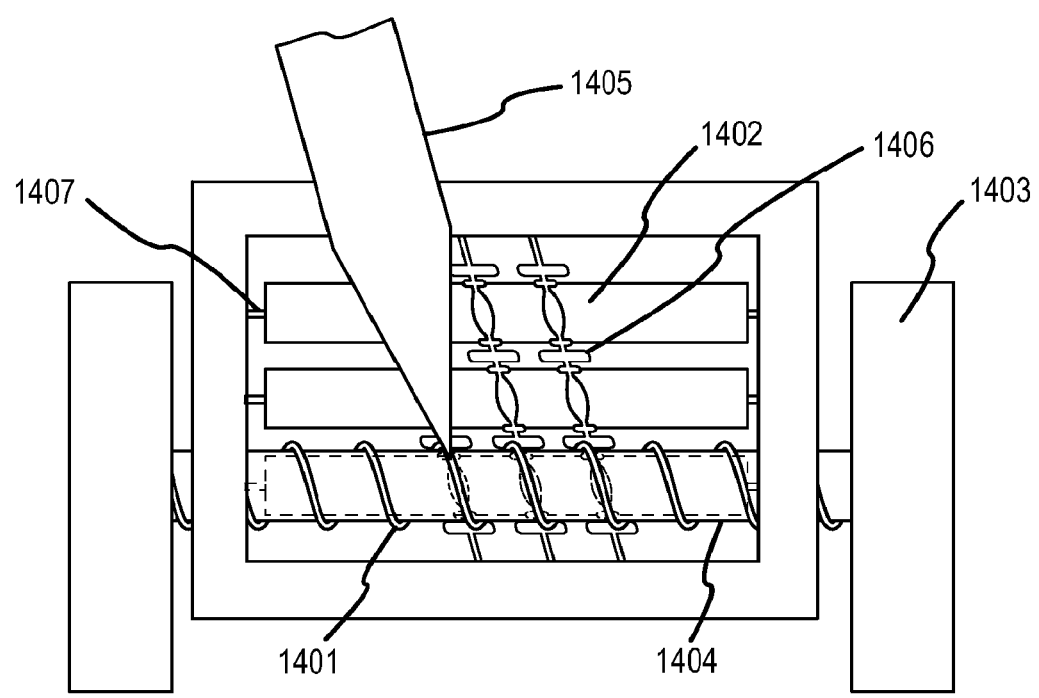
FIG. 14 illustrates an welding fixture for assembling an actuator lattice onto a coil skeleton spring to fabricate a MicroFlex instrument.

Assembly of flat photo-etched components into a strong, three-dimensional device is difficult at small scales. As such, a novel method that is both simple and suitable for parallel automation at reduced costs was developed in accordance with another aspect of the invention. However, the actuated coil segments of the invention are not so limited. With reference to FIG. 14, a method for fabrication an actuated coil segment of the invention is illustrated. The SMA actuator lattice 1402, along with an optional welding strip 1406, is positioned over the welding mandrel 1403, which is inserted into the preformed skeleton spring 1401, axially stretched to the assembly length, and clamped with compression rings 1403 at each end. The welding stylus 1405 is positioned over the assembly at desired locations, and spot welds are produced by a resistance welder, whose electrodes are connected to the welding mandrel 1403, and the welding stylus 1405. Welds between the skeleton spring and the actuator lattice occur where they contact under pressure between the mandrel and stylus. By repositioning the stylus laterally, a series of welds are produced along the skeleton axis, attaching one actuator string to the skeleton.

Then, the copper mandrel is rotated to wrap the actuator lattice around the skeleton spring, and to position the welding electrodes at the required positions for attaching the next string of actuators to the skeleton. After each string is welded to the skeleton, one welding electrode is connected to the SMA handling frame, so that when the mandrel is energized, current flows laterally through the handling frame, fusing anchor links 1407 to release the actuator strings from their handling frame.

When all actuator strings are welded to the skeleton and released from the handling frame, the axial spring tension is released, thereby allowing the axial tension in the SMA coil skeleton to compress the plurality of SMA actuator elements inward, resulting in compressed-state coil actuators in each coil segment.

Figure 15:
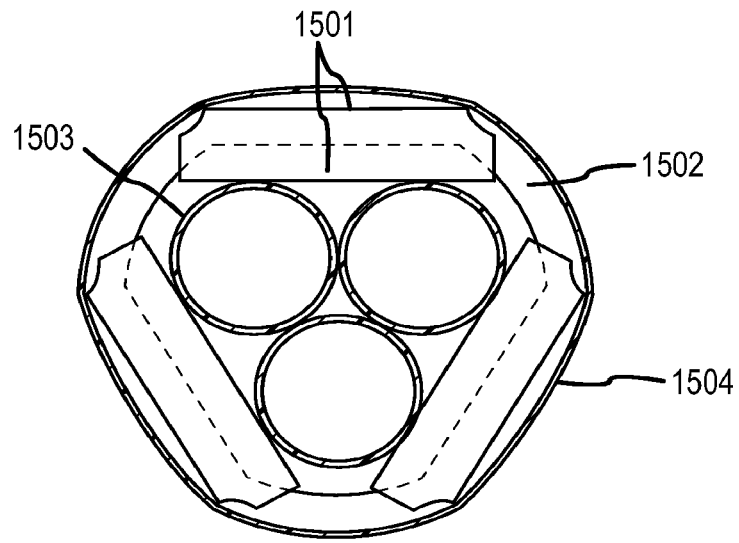
FIG. 15 illustrates a cross section of a three port MicroFlex instrument.
Figure 16:
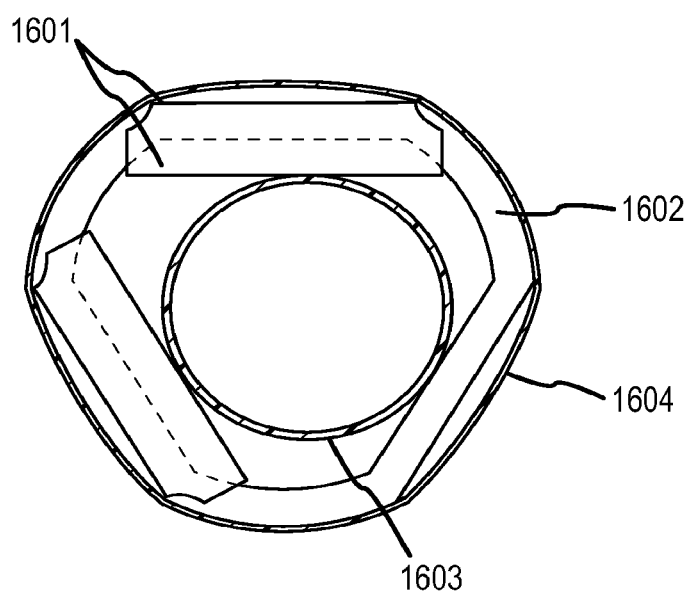
FIG. 16 illustrates a cross section of a one-port MicroFlex instrument.

Since the actuator elements then reside on the exterior of the coil skeleton, the electrical continuity of bus connections may be verified, and the SMA/heater/sensor/demultiplexer assembly may be visually inspected for any damage induced by the rolling weld assembly process. In certain embodiments, the process may result in two strings of actuated coil segments including a plurality of elements each. In other embodiments, three strings of actuated coil segments may be included. FIG. 15 shows a cross section of the three-string assembly which has three actuator elements 1501 in each turn of the three-faceted skeleton spring 1502. This embodiment provides three interior ports 1503, and also indicates an exterior welding band 1504, which would be necessary for a non-superelastic skeleton spring. FIG. 16 shows a two-string variant, with components corresponding to FIG. 15, which allows a relatively large single interior port compared to the device outside diameter.

IV. MFS Control System

Figure 17:
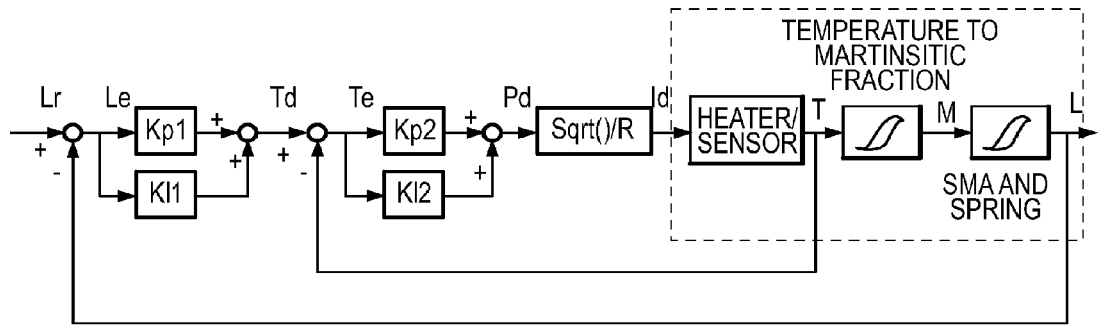
FIG. 17 shows a block diagram of a temperature and strain feedback control system for tracking of operator motion commands.

In another aspect of the invention, a novel control system is provided, which is able to address both temperature hysteresis and strain hysteresis behavior The control system is generally configured to monitor and control actuation of individual actuator elements based at least in part on feedback of sensed temperature and strain from the heater/sensor layers in each actuator to an applied heater current. FIG. 17 shows a block diagram of the control system, where the physical portion of the systems is indicated by the dotted box. The control system contains two loops. The inner loop measures temperature T from the resistance of the series connection of heater elements bonded to the corresponding actuator, based on a calibration of the heater element temperature coefficient of resistance (TCR). This measurement is combined with the desired temperature Td in a proportional-integral control loop to force the actuator temperature to track the desired value. This loop compensates for the temperature hysteresis in the SMA actuator, which would otherwise cause the internal state of the actuator, described by the so-called martensitic fraction, to lag behind the desired value with a detrimental effect on actuator positioning speed and accuracy.

Figure 18:
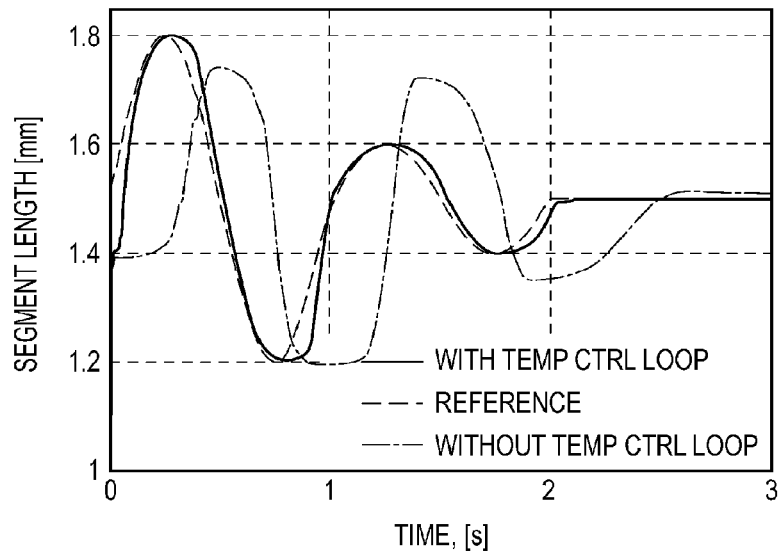
FIG. 18 shows an example of the performance of a control system numerical simulation with and without temperature feedback.
Figure 19:
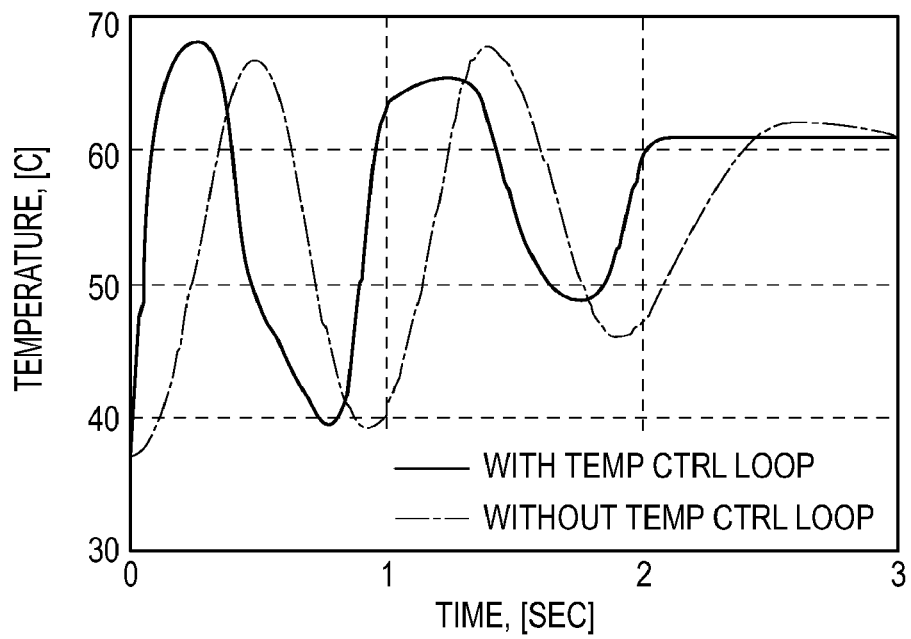
FIG. 19 shows the temperature excursions obtained during the tracking simulation of FIG. 18.
Figure 20:
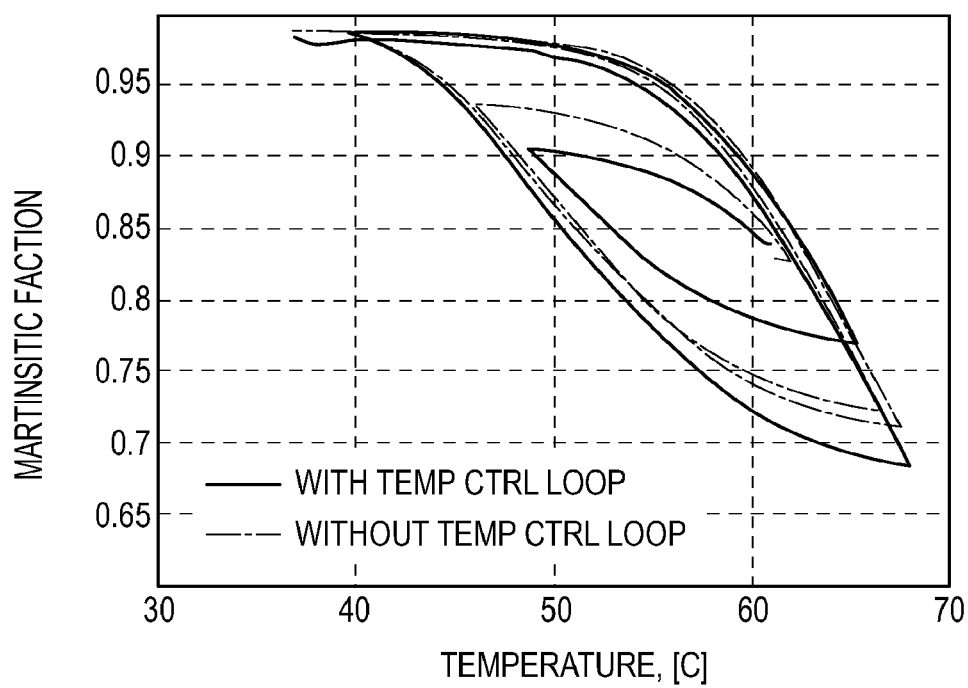
FIG. 20 shows the temperature hysteresis present in the shape memory alloy model used in the simulation of FIG. 18.

The outer loop in FIG. 17 measures actuator position by transducing bending strain in the heater/sensor layer to a voltage division ratio in the series connection of heater elements which is proportional to SMA layer strain. This measured position L is then compared to the desired reference position Lr in another proportional-integral control loop to force L to track Lr. FIG. 18 shows the results of a detailed simulation of this control system tracking a varying position reference Lr which is representative of motions that may be required in a surgical procedure. Note that the tracking error is very small, and the static accuracy at the end of the motion is very good for the combined strain and temperature control system. Tracking is poor with the strain feedback loop alone. FIG. 19 shows the corresponding SMA temperature excursions during tracking, indicating the combination of temperature and strain feedback provides superior tracking performance without substantial increases in temperature excursion. FIG. 20 shows the temperature hysteresis present in the physical model in these simulations, which is representative of measured behavior in SMA materials.

Figure 21:
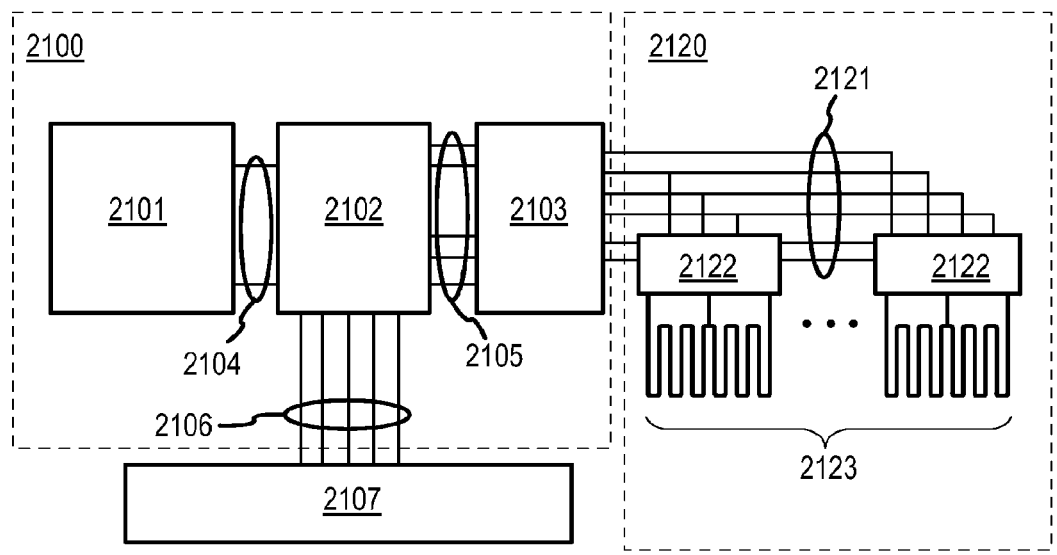
FIG. 21 shows an example embodiment of the electronics used to implement the control system of FIG. 17.

Any suitable electronics may be used to implement the temperature and strain control loops of the invention. The electronics should be capable of interfacing with the demultiplexing circuits and parallel bus(es) of the actuator elements, as well as to a suitable user control interface. Either analog or digital control may be utilized By way of example, FIG. 21 shows an overall system diagram of one embodiment of the invention. As shown in FIG. 21, the control system 2100 may comprise a computer based Controller 2101, and A/D Digital I/O Card 2102, and a Custom Bus Driver Board 2103. Controller 2101 may interface with Card 2102 via I/O Bus 2104, and Card 2102 may interface with Driver 2103 via 2 A/D, 2 Dig Out, and Ground bus 2105. Further, Card 2102 may also interface with a User Control Interface 2107 via, e.g., 4 A/D and Ground bus 2106. Driver 2103 interfaces with Demultiplexing Chips 2122 via multi-wire bus 2121, and Demultiplexing Chips 2122 are interfaced with the Integrated Heater/Sensor Layer 2123 bonded to actuator elements of an MFS System 2120.

V. MicroFlex Scope (MFS) Apparatus and Methods of Use

As discussed above, in another aspect of the invention, an MFS apparatus is provided which comprises at least one actuated structural skeleton. More generally, an MFS apparatus of the invention is a microdexterous endoscope apparatus which comprises a manipulatable catheter. The catheter includes a lumen comprising at least one port in the interior of the lumen and at least one actuated structural skeleton at the distal end of the catheter. As described above, the actuated structural skeleton generally comprises a plurality of indirectly heated shape memory alloy (SMA) actuators secured to a SMA structural skeleton, wherein each SMA actuator is adapted to exhibit a variation in bend state corresponding to a variation in temperature of the SMA actuator. In certain embodiments, the actuated structural skeleton is an actuated coil segment comprising at least one port in the interior of the actuated coil segment.

The MFS may further comprise a control system configured to monitor and control actuation of the actuated structural skeleton(s), e.g., by monitoring and controlling at least one coil segment, based at least in part on, e.g., temperature and strain feedback from the actuated structural skeleton(s). The MFS also includes an electrical bus traversing the length of the catheter, which electrically interfaces with the at least one actuated structural skeleton and the control system. In certain embodiments, the control system may be adapted to modulate application of a current to thereby independently control the temperature of the plurality of SMA actuators to achieve a desired bend state based at least in part on a non-linear hysteresis control model using feedback voltages obtained from the SMA actuator via the electrical bus.

The MFS may be controlled by a user via a stylus attached to the base of the endoscope instrument. Motion of the stylus provides commands to a control system, which provides current to heat actuator elements in the MFS tip, causing the tip to track stylus motions. The four wire sensor/actuator bus and associated demultiplexing chips at each actuator allow for control of the position of many actuator segments in the MFS tip without requiring a large number of connecting wires along the length of the MFS catheter.

By way of example, FIG. 1 shows an enlarged view of one embodiment of an MFS of the invention as it might be used to visualize and biopsy a small lesion in a body lumen. The distal end of the device 100 contains several actuator segments 102, that can bend under the command of the operator, extending 102' (upon heating) or contracting 102"(upon cooling) the structural skeleton at each segment. This gives the distal end snake-like dexterity to angulate in any direction and access the body lumen ahead and to the sides of the catheter tip with fine control over tip position and applied tissue forces. In the exemplified embodiment, the MFS will have three ports. One port 104 may, e.g., contain an optical fiber scope for direct visualization. A second port 109 may serve as a tool port (e.g., 110 biopsy brush, knife, curette, rotary burr, laser cautery, etc.), and a third port 105 may support vacuum/flush procedures, e.g., to remove tissue fragments or to clean the fiber scope lens. In this embodiment, the tool is dextrously manipulated by the actuated distal end. Smaller optical fibers 106 may be included within the lumen of the MFS to provide illumination of the visual field. Further, an optional inflatable cuff 110 and inflation tube 108 may be used to stabilize the tip, distend tissue for better access, localize lavage fluids, etc. Electrical connection to sense and control actuator elements is provided by a multi-wire cable 107. An insulated sheath 101 encapsulates the catheter.

FIG. 2 illustrates an alternative embodiment of an MFS of the invention, as it might be used to navigate a body lumen and to manipulate tissue in distant cavities, e.g. in the sinuses. The distal end 201 of the device 200 contains three ports 203, 204, 205 surrounded by several actuator elements 202 that can individually bend under the command of the operator. Again, this gives the tip snake-like dexterity to provide fine tool control for access to tissue in the center of the passage, as well as on the sides. In certain embodiments, the actuators may be spaced along the length of the catheter at predetermined locations such that the proximal portions of the catheter follow the same path as the distal end of the catheter. The control system may be configured so as to facilitate such actuation of the proximal portions to follow the distal end of the catheter. In this embodiment, all three ports are angulated with the actuator segments, moving the tool (e.g., in port 204) together with the field of view (e.g., an image guide in port 203), as well as an auxilliary port 205 which may be used for a second tool, vacuum/flush, etc.

In certain embodiments, the ultra-flexible distal end of the MFS may be controlled by an operator using a manipulative such as a stylus. Motion of the stylus produces commands for the actuators of the MFS through a computer control system. The control system senses actuator element position (e.g., bend state) and causes heating in the element to produce bending motion. This causes the flexible tip, e.g., as seen through the image guide 104 in the remote visual field, to follow the stylus motion caused by the operator's hand. Alternatively, the field of view is moved by the stylus, e.g. as in the device 200. Various tools may be inserted through the tool ports (109 or 204, 205) during a procedure to enable a wide variety of diagnostic and therapeutic options Further, as shown in FIG. 2, the image guide (e.g., in port 204) may be the limiting factor in the MFS catheter flexibility. As such, in certain embodiments, e.g., FIG. 1, the image guide 104 may terminate at the proximal side of the distal end of the catheter, leading to a configuration wherein only the tool port 109, and not the image guide, passes through the distal end of the ultra-flexible tip.

Figure 3:
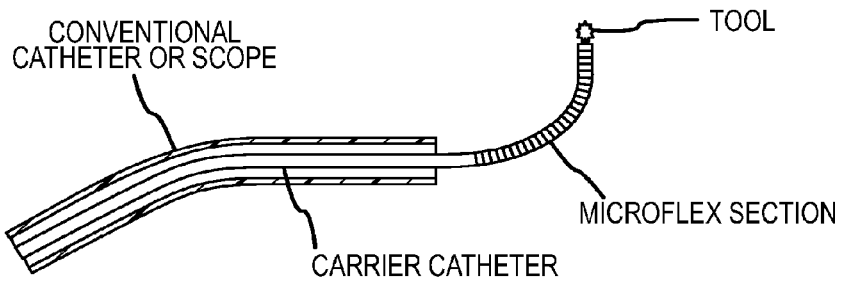
FIG. 3 illustrates a MicroFlex Tool variation of the invention, where a tool is permanently affixed to the actuated cathether, and this is inserted into a conventional catheter or endoscope.

Another embodiment of the MicroFlex technology is shown in FIG. 3, where the actuated skeleton does not contain a leumen. Instead, a tool is fixed to the distal tip. The resulting MicroFlex Tool (MFT) may be inserted into a conventional catheter or scope tool port, providing a highly dextrous appendage at the tip for tissue sampling or manipulation. Another MicroFlex Tool, e.g., a knife, may be substituted by withdrawing the first tool and inserting the second. This provides the simple, low cost, disposable MicroFlex capability.

Figure 4:
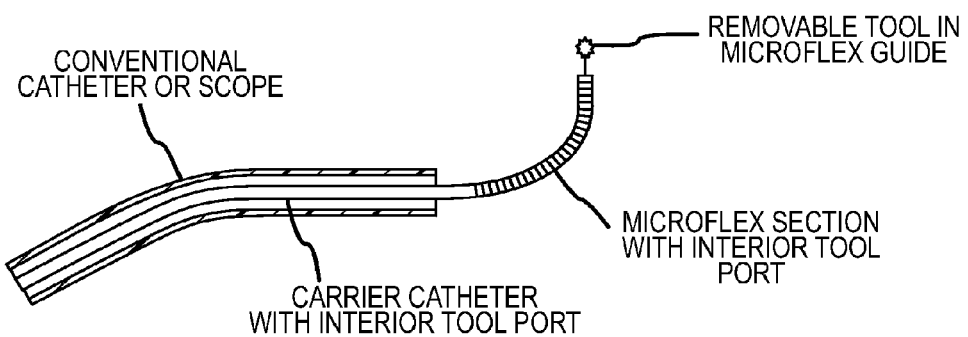
FIG. 4 illustrates a MicroFlex Tool Guide variation, where the actuated catheter contains a single port for a disposable tool.

A MicroFlex Guide (MFG) embodiment is shown in FIG. 4, where the MFG contains a single lumen for a removable tool. This enables the MFG component to be reused, if desired, and supports a variety of disposable tools. The MFG may be inserted into the tool port of a conventional scope, which provides the image guide needed for visualization during manipulation of the ultra flexible tool guide.

Figure 5:
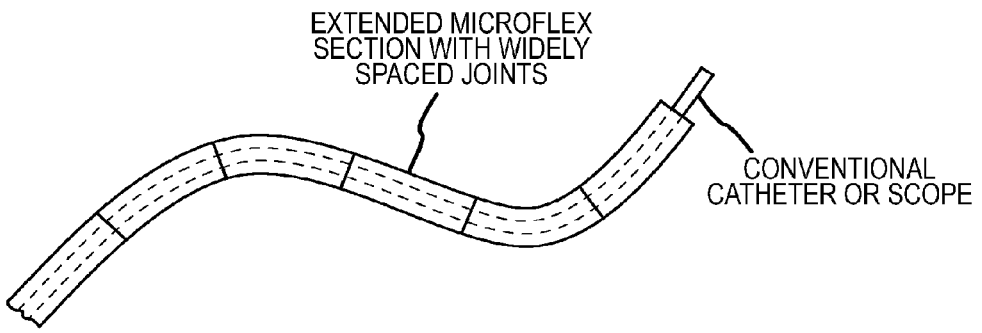
FIG. 5 illustrates a MicroFlex Scope Guide variation, where the actuated catheter contains a single large port to guide a conventional catheter or endoscope.

The MicroFlex Scope Guide (MFSG) embodiment is illustrated in FIG. 5. This enables conventional scope or catheter to bend more dextrously by providing actively controlled joints along the length of the scope, or only at the tip, depending on the intended application. Here the MFSG has a single large lumen, through which the conventional scope or catheter is inserted. Once inserted into the body, the MFS Scope Guide can provide a fixed passageway for fast re-insertion of a variety of different catheters or tools.

Figure 6:
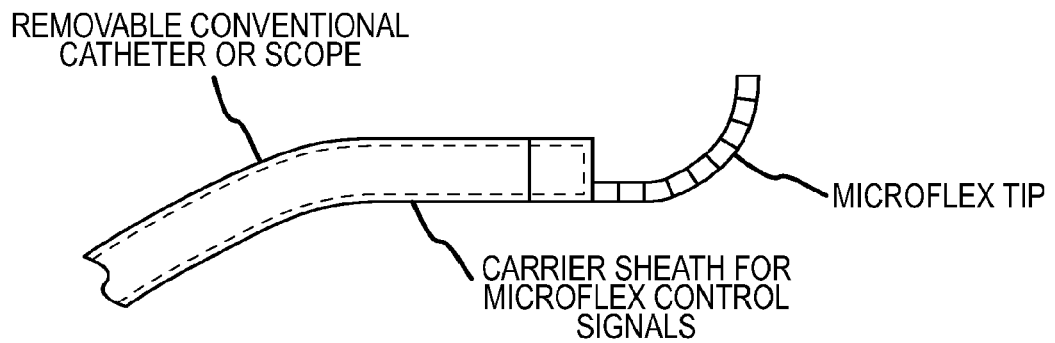
FIG. 6 illustrates a MicroFlex Tip containing an ultra-flexible actuated tip that can be added to a conventional catheter or scope without significantly increasing the instrument diameter.

FIG. 6 shows another embodiment, where a MicroFlex Tip provides a large lumen for insertion of a conventional scope or catheter in a non-actuated sheath, which enables a highly dexterous tip to be added to a standard scope with little change in outside diameter, extending the capability of existing scopes into new areas or new procedures.

Since the working components of the MFS device will be sealed against contact with tissue, sterilization will generally be an issue primarily with the tool and flush ports. These ports are small, but can be force-flushed with sterilization solution prior to re-use. Further, inserted tools may generally be disposable or sterilized separately prior to use.

In particular embodiments, a MFS apparatus of the invention may be used in sinus surgeries; lung and airway diagnosis, sampling and treatment; and other endoscopic diagnostic, treatment and surgical procedures known in the art. For instance, the methods of the present invention are useful in neurosurgery, urology, respiratory care, chemoprevention, pediatrics, neonatology, and other ENT applications.

In one embodiment, a MFS of the invention may be used in sinus applications to support direct visualization and access for diagnostic, treatment, and surgical procedures. In such embodiments, the diameter of the MFS endoscope will, e.g., be about 3 mm. In other embodiments, a MFS of the invention may used in lung and airway applications to support direct visualization and access for diagnostic, treatment and surgical procedures. For instance, the MFS may used in canulating and sampling for biopsy in an accurate manner so as prevent perforation of the bronchi. In such embodiments, the diameter of the MFS endoscope will, e.g., be about 1 mm.

In one embodiment, the MFS of the invention may be used in a diagnostic method for the identification of endobronchial lesions. As described herein, the MFS of the invention enables access into the peripheral airways thereby enabling direct visualization and sampling of lesions. Further, the MFS of the invention provides a novel platform, e.g., via the tool port, for application of laser therapy, brachytherapy, localized chemotherapy, electrocautery, cryotherapy, photodynamic therapy, placement of airway stents, and balloon dilatation to relieve airway obstruction caused by malignant and benign airway lesions.

In sum, while a number of surgical instruments have facilitated endoscopic procedures, without intending to be limited by theory, the MFS technology offers several distinct advantages that improve the quality of care, including: (i) support of direct visualization, access, and real-time imaging; (ii) access to previously inaccessible regions of the body; (iii) improved maneuverability and precise positioning; (iv) active controlled tip which supports a variety of tools; and/or (v) minimization of complications and postsurgical morbidity by supporting precise surgery and minimal trauma to the body cavities, e.g., nasal structures and airway passages.

EXAMPLES

Example 1

Direct Visualization

An investigation of the optical quality provided by the image guide in the catheter has been conducted. In one run, a 1.0 mm nominal outside diameter of a fiber bundle, consisting of fibers approximately 4 µm in diameter, supporting approximately 30,000 fibers was used for image transmission. Lenses on the fiber tip can provide a depth of field from 1 mm up to 10 mm, with an angular field of view of 55 degrees. The bending radius of these image guides is as small as 30 mm.

Figure 22:
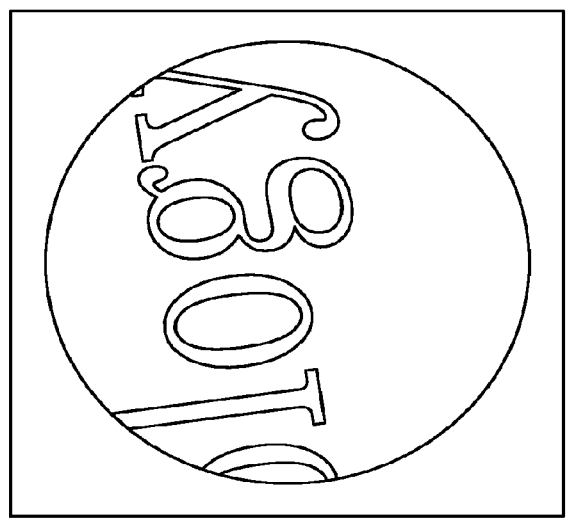
FIG. 22 illustrates an exemplary direct visualization capability of an image guide in accordance with an embodiment of the invention.

Another experiment was constructed with approximately 3000 image guide fibers, surrounded by an illumination fiber ring. FIG. 22 shows an image recorded with this scope, taken at a distance of approximately 5 mm from a printed target. The ink letters are approximately 2 mm high, and are clearly identifiable. When magnified in a still image like this, individual fiber pixels are visible, and the image becomes noticeably grainy. However, this pixilation is reduced considerably in live video images, due to image motion across the fibers, resulting in a sharper apparent image. In both cases, review by a pulmonary medical advisor indicated that this resolution should meet, e.g., bronchial mucosa exam requirements.

Lenses on the fiber tip can provide a depth of field from 1 mm to 10 mm, with an angular field of view of 55 degrees. This field of view can be canted to support visualization of the sides of the passage by combining a small prism with the distal lens. The bending radius of these image guides is as small as 10 mm, which is smaller than the bend radius of the conventional bronchoscope through which the MFS passes, and is suitable for navigating the branches of the many body cavities including the peripheral airways. As described above, the image guide may be the limiting factor in the MFS catheter flexibility, leading to an embodiment wherein only the tool, and not the image guide, passes through the most distal end of the ultra-flexible tip (see FIG. 1).

Example 2

Clearing Secretions and Blood

Clinicians routinely employ proven methods such as saline flush and administration of selected drugs to thin mucous, decrease secretions and minimize bleeding during procedures. Recent clinical studies employing fluorescence imaging techniques have refined these secretion reduction techniques. A flush/suction port has been incorporated into certain embodiments of the MFS design and located close to the distal lens of the image guide to clear material on or in front of the lens.

| SAMPLE | SUCTION RATE (seconds/ml) |
| --- | --- |
| Saline | 22 |
| Saline/Airway Secretion (1:1 Mix) | 29 |
| Saline/Whole Blood (1:1 Mix) | 42 |

As shown in the table above, testing conducted with a sample small diameter catheter suitable to fit within the MFS demonstrated the feasibility of removing blood and airway secretions through this port. Secretion samples at room temperature were removed from the catheter using Standard Wall Suction, used for bronchoscopy, with saline aspiration between each test to clear the tubing. Assuming the use of appropriate procedures to flush and thin secretions, the removal rate for all substances should be more than adequate to handle the typical 0.1-0.3 ml bleeding encountered in a distal airway. This testing demonstrates that the MFS flush/suction port should be able to clear small amounts of airway secretions and blood away from the tip of the instrument in distal airways.

Example 3

Prototype Model Actuated Coil Segment

A method similar to that described with reference to FIG. 15 was used to generate a prototype device in stainless steel steal. Such prototype assembly uses a technique that first rolls and spot welds the actuator element strings over a coil spring skeleton, using a copper stylus rail system and copper mandrel as resistance welding electrodes, selectively energized to produce welds at the points where they cross. FIG. 11 shows a model in stainless steel constructed by similar process. When the welds are complete, the coil ends are released from their fixtures, allowing the axial tension in the coil to compress the actuator elements inward, resulting in a final structure as illustrated in FIG. 1.

The invention has now been described in detail. However, it will be appreciated that the invention may be carried out in ways other than those illustrated in the aforesaid discussion, and that certain changes and modifications may be practiced within the scope of the appended claims. Accordingly, the scope of this invention is not intended to be limited by those specific examples, but rather is to be accorded the scope represented in the following claims.

What is claimed is:

1. An actuator element comprising:
   a shape memory alloy (SMA) layer having a first, and second end, the SMA layer having a biasing spring operatively associated therewith, the spring biasing the layer from a planar configuration to a select bend between the first and second end at a reference state by a spring force, the SMA layer being adapted to exhibit a variation in bend state corresponding to a variation in temperature of the SMA layer, there being a thermal conduction barrier between adjacent SMA actuator layers;
   an integrated heater/sensor layer interfaced with said SMA layer, wherein said heat/sensor layer is adapted to indirectly heat the SMA layer upon application of current to the heater/sensor layer, to sense the temperature and bend state of the SMA layer, and to produce a voltage in proportion to the sensed temperature and bend state of the SMA layer; and
   a demultiplexing circuit and parallel bus interfaced with said heater/sensor layer, wherein said multiplexing circuit and parallel bus are adapted to allow for connection of multiple actuator elements thereby enabling communication and control of individual actuator elements when multiplexed with a plurality of actuator elements.

2. The actuator element of claim 1, wherein the parallel bus comprises a multi-wire flex cable bus system configured to interconnect multiple actuator elements.

3. The actuator element of claim 1, further comprising an exterior insulation sheath adapted to minimize exposure of tissue to electrical current or elevated temperatures when used in vivo.

4. The actuator element of claim 1, wherein the exterior surface of said SMA layer is at least partially interfaced with a closed circuit cooling system configured to provide a chilled bias temperature state to the SMA layer.

5. The actuator element of claim 1, wherein said SMA layer comprises a NiTi alloy with a bend state activation temperature between 17 deg C. and 67 deg C.

6. The actuator element of claim 1, wherein the heater/sensor layer interfaces with the SMA layer via a strain-isolating adhesive layer.

7. The actuator of claim 1, wherein the heater/sensor layer comprises two metal layers separated by a dielectric layer, capable of heating and sensing temperature.

* * * * *